United States Patent
Kent et al.

(10) Patent No.: US 9,492,667 B1
(45) Date of Patent: Nov. 15, 2016

(54) SYSTEMS AND METHODS FOR CLOSED LOOP NEUROSTIMULATION

(71) Applicant: Pacesetter, Inc., Sunnyvale, CA (US)

(72) Inventors: Alexander Kent, Mountain View, CA (US); Edward Karst, Los Angeles, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/844,380

(22) Filed: Sep. 3, 2015

(51) Int. Cl.
*A61N 1/36* (2006.01)

(52) U.S. Cl.
CPC ....... *A61N 1/36139* (2013.01); *A61N 1/36071* (2013.01)

(58) Field of Classification Search
None
See application file for complete search history.

(56) References Cited

U.S. PATENT DOCUMENTS

| | | | |
|---|---|---|---|
| 5,919,216 A * | 7/1999 | Houben | A61B 5/14532 607/72 |
| 7,212,110 B1 | 5/2007 | Martin et al. | |
| 7,228,179 B2 | 6/2007 | Campen et al. | |
| 7,571,007 B2 | 8/2009 | Erickson et al. | |
| 8,478,389 B1 * | 7/2013 | Brockway | A61B 5/7203 600/509 |
| 9,054,436 B2 | 6/2015 | Boogaard et al. | |
| 2006/0170486 A1 | 8/2006 | Erickson et al. | |
| 2009/0326608 A1 | 12/2009 | Erickson et al. | |
| 2010/0152808 A1 * | 6/2010 | Boggs, II | A61N 1/0456 607/46 |
| 2011/0257708 A1 * | 10/2011 | Kramer | A61N 1/36114 607/62 |
| 2014/0031905 A1 * | 1/2014 | Irazoqui | A61N 1/36189 607/73 |
| 2014/0343564 A1 | 11/2014 | Feler et al. | |

FOREIGN PATENT DOCUMENTS

| | | |
|---|---|---|
| WO | 01/93953 A1 | 12/2001 |
| WO | 2012155188 A1 | 11/2012 |

\* cited by examiner

*Primary Examiner* — Kennedy Schaetzle
(74) *Attorney, Agent, or Firm* — Theresa A. Raymer

(57) ABSTRACT

Systems and methods to control non-paresthesia stimulation of nerve tissue of a patient are herein disclosed. The systems and methods deliver a non-paresthesia stimulation waveform to at least one electrode proximate to target nerve fibers, and define an analysis window that is positioned to occur at an intermediate point within at least one of a first burst or an inter-burst delay. Additionally, the systems and methods, during the analysis window, measure evoked potential (EP) signals from the target nerve fibers. The systems and methods also analyze the EP signals to obtain activity data for select nerve fiber components, and adjust at least one therapy parameter to change the non-paresthesia stimulation waveform based on the activity data.

20 Claims, 15 Drawing Sheets

SYSTEMS AND METHODS FOR CLOSED LOOP NEUROSTIMULATION

BACKGROUND OF THE INVENTION

Embodiments of the present disclosure generally relate to neurostimulation (NS) systems, and more particularly to systems and methods for closed loop spinal cord stimulation (SCS) controlling non-paresthesia stimulation of nerve tissue of a patient.

NS systems are devices that generate electrical pulses and deliver the pulses to nerve tissue to treat a variety of disorders via one or more electrodes. For example, SCS has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses depolarize neurons and generate propagating action potentials into certain regions or areas of nerve tissue. The propagating action potentials effectively mask certain types of physiological neural activity, increase the production of neurotransmitters, or the like.

SCS devices apply electrical energy to the spinal cord. Conventionally, the SCS corresponds to a series of continuous pulses at around 50 Hz forming a "tonic waveform" to stimulate the nerve tissue of a patient inducing "paresthesia" (a subjective sensation of numbness or tingling by the patient) in the afflicted bodily regions. Inducing this artificial sensation replaces the feeling of pain in the body areas effectively masking the transmission of non-acute pain sensations to the brain.

Recently, SCS devices have begun using a non-paresthesia stimulation waveform such as a "burst waveform" to relieve pain symptoms within the afflicted bodily regions instead of the tonic waveform. The burst stimulation waveform has bursts of multiple stimulation pulses, and these bursts are separated by inter-burst delay periods in which no stimulation is applied. Unlike the tonic waveform, SCS using the burst waveform may not generate paresthesia. However, due to the lack of paresthesia, there may be a loss of patient feedback regarding the location and strength of stimulation. Due to this loss of patient perception, there may be a greater risk of over-stimulation when the NS system moves with respect to the spinal cord during movement of the patient.

During stimulation by the NS systems, evoked potentials are emitted from the stimulated nerve tissue. It has been proposed that the NS system may measure the evoked potential for a feedback mechanism to adjust the SCS. The evoked potential signals may be generated by neuronal transmembrane currents of neurons activated following or in response to the SCS. The evoked potential signals propagate within the population of sensory nerve fibers through subsequent orthodromic or antidromic propagation from the excitation site. SCS using the tonic waveform results in the simultaneous activation of multiple neurons, which generate a signal of sufficient amplitude for recording. However, SCS using the burst waveform may not simultaneously activate the multiple neurons. For example, during the burst waveform one or more neurons may be activated at different times. This can result in an evoked potential signal lacking coherent neuronal activation, which may hinder recording of the evoked potential and use of feedback mechanisms for closed loop adjustment of SCS.

A need exists to overcome the shortcomings of traditional recording of evoked potential signals generated from stimulation using burst waveforms.

SUMMARY

In accordance with one embodiment, a method to control non-paresthesia stimulation of nerve tissue of a patient is provided. The method may include delivering a non-paresthesia stimulation waveform to at least one electrode located proximate to target nerve fibers. The non-paresthesia stimulation waveform includes pulses arranged in at least first and second bursts separated by an inter-burst delay. The pulses excite at least a portion of the corresponding target nerve fibers that enter a refractory state after being excited and firing action potentials. The method may also include defining an analysis window that is positioned to occur at an intermediate point within at least one of i) the first burst or ii) the inter-burst delay. The analysis window is positioned to overlap at least a trailing portion of the refractory state induced by the associated preceding pulses. Additionally, the method may include measuring evoked potential (EP) signals during the analysis window from the target nerve fibers. The EP signals are generated in response to the pulses of the first burst. Further, the method may include analyzing the EP signals to obtain activity data for select nerve fiber components and adjusting at least one therapy parameter to change the non-paresthesia stimulation waveform based on the activity data.

In an embodiment, a system to control non-paresthesia stimulation of nerve tissue of a patient is provided. The system may include an implantable pulse generator (IPG) electrically coupled to a first electrode. The IPG is configured to deliver non-paresthesia stimulation waveform to at least one electrode located proximate to target nerve fibers. The non-paresthesia stimulation waveform includes pulses arranged in at least first and second bursts separated by an inter-burst delay. The pulses excite at least a portion of the corresponding target nerve fibers that may enter a refractory state after being excited and firing action potentials. The system may also include a memory device configured to store programmed instructions and a processor. The processor may execute the programmed instructions to perform operations. The operations may include defining an analysis window that is positioned to occur at an intermediate point within at least one of i) the first burst or ii) the inter-burst delay. The analysis window is positioned to overlap at least a trailing portion of the refractory states induced by the associated preceding pulses. The operations further include measuring evoked potentials (EP) signals during the analysis window from the target nerve fibers. The EP signals are generated in response to the pulses of the first burst. Further, the operations further may include analyzing the EP signals to obtain activity data for select nerve fiber components and adjusting at least one therapy parameter to change the non-paresthesia stimulation waveform based on the activity data.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Various embodiments described herein include a method and/or system for a closed loop spinal cord stimulation based on a novel approach for recording neuronal evoked potential (EP) signals during a non-paresthesia stimulation waveform for spinal cord stimulation (SCS) and for using the EP signals in a closed loop neurostimulation (NS) system.

Figure 1:
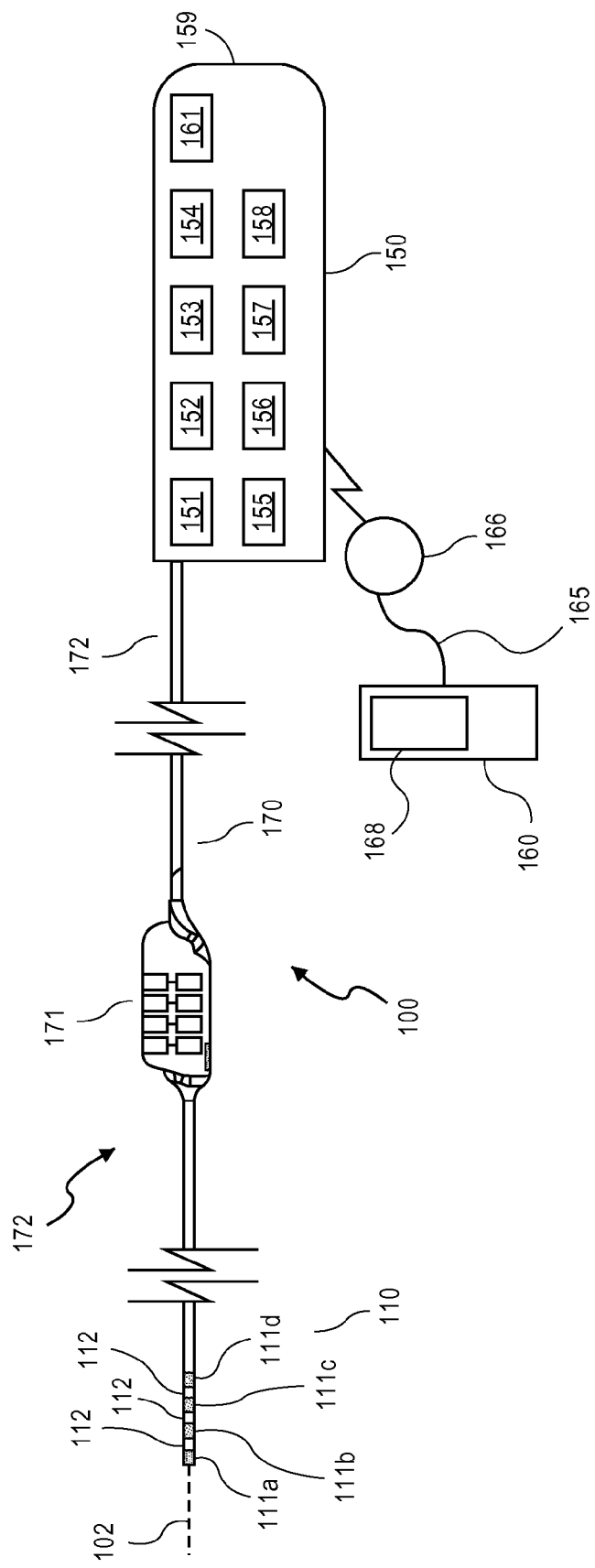
FIG. 1 illustrates a neurostimulation system, according to an embodiment of the present disclosure.

FIG. 1 depicts a NS system 100 that generates electrical pulses that form a non-paresthesia stimulation waveform (e.g., burst waveform) for application on tissue of a patient according to one embodiment. For example, the NS system 100 may be adapted to stimulate spinal cord tissue, dorsal root, dorsal root ganglion, peripheral nerve tissue, deep brain tissue, cortical tissue, cardiac tissue, digestive tissue, pelvic floor tissue, or any other suitable nerve tissue of interest within a patient's body.

The NS system 100 includes an implantable pulse generator (IPG) 150 that is adapted to generate electrical pulses for application on the stimulation target, such as target nerve fibers of a patient. The IPG 150 typically comprises a metallic housing or can 159 that encloses a controller 151, pulse generating circuitry 152, a charging coil 153, a battery 154, a far-field and/or near field communication circuitry 155, battery charging circuitry 156, switching circuitry 157, sensing circuitry 158, memory 161 (e.g., a tangible and non-transitory computer readable storage medium, such as ROM, RAM, EEPROM, and/or the like). For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference.

The IPG 150 may comprise a separate or an attached extension component 170. If the extension component 170 is a separate component, the extension component 170 may connect with a "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 may include a multiplexer and/or other switching devices, and directs the electrical pulses to corresponding electrodes 111a-d of one or more leads 110. The switching circuitry 157 connects to outputs of the IPG 150.

Electrical connectors (e.g., "Bal-Seal" connectors) within the connector portion 171 of the extension component 170 or within the IPG header may be employed to conduct various pulses that form the non-paresthesia stimulation waveform. The terminals of the one or more leads 110 are inserted within the connector portion 171 or within the IPG header for electrical connection with respective connectors. Thereby, the pulses forming the non-paresthesia stimulation waveform originating from the IPG 150 are provided to the one or more leads 110. The pulses are then conducted through the conductors of the lead 110 and applied to target nerve fibers of a patient via electrodes 111a-d. Any suitable known or later developed design may be employed for connector portion 171.

The electrodes 111a-d may be positioned along a horizontal axis 102 of the lead 110, and are angularly positioned about the horizontal axis 102 so the electrodes 111a-d do not overlap. The electrodes 111a-d may be in the shape of a ring such that each electrode 111a-d continuously covers the circumference of the exterior surface of the lead 110. Each of the electrodes 111a-d are separated by non-conducting rings 112, which electrically isolate each electrode 111a-d from an adjacent electrode 111a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The electrodes 111a-d may be configured to emit the pulses in an outward radial direction proximate to or within a stimulation target. Concurrently while emitting the pulses and/or separately, the electrodes 111a-d may also be configured to acquire electrical potential measurements (e.g., voltage, current) for the sensory circuit 158, such as evoked potentials generated from the target nerve fibers. Optionally, the IPG 150 may have more than one lead 110 connected via the connector portion 171 of the extension component 170 or within the IPG header.

Additionally or alternatively, the electrodes 111a-d may be in the shape of a split or non-continuous ring such that the pulse may be directed in an outward radial direction adjacent to the electrodes 111a-d. Examples of a fabrication process of the electrodes 111a-d is disclosed in U.S. Pat. No. 9,054,436, entitled, "METHOD OF FABRICATING STIMULATION LEAD FOR APPLYING ELECTRICAL STIMULATION TO TISSUE OF A PATIENT," which is expressly incorporated herein by reference. It should be noted the electrodes 111a-d may be in various other formations, for example, in a planar formation on a paddle structure as disclosed in U.S. Patent Publication No. 2014/0343564, entitled, "PADDLE LEADS FOR NEUROSTIMULATION AND METHOD OF DELIVERING THE SAME," which is expressly incorporated herein by reference.

The lead 110 may comprise a lead body 172 of insulative material about a plurality of conductors within the material that extend from a proximal end of the lead 110, proximate to the IPG 150, to its distal end. The conductors electrically couple a plurality of the electrodes 111a-d to a plurality of terminals (not shown) of the lead 110. The terminals are adapted to receive electrical pulses and the electrodes 111a-d are adapted to apply the pulses to the stimulation target of the patient. Also, sensing of physiological signals may occur through the electrodes 111a-d, the conductors, and the terminals. It should be noted that although the lead 110 is depicted with four electrodes 111a-d, the lead 110 may include any suitable number of electrodes 111a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for all embodiments, the lead body 172 of the lead 110 may be fabricated to flex and elongate upon implantation or advancing within the tissue (e.g., nervous tissue) of the patient towards the target nerve fiber and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," and U.S. Patent Publication No. 2012/0110846 entitled "COMPLIANT ELECTRICAL STIMULATION LEADS AND METHODS OF FABRICATION," each of which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different electrodes 111a-d may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., non-paresthesia stimulation) that include generated and delivered stimulation pulses through various electrodes of one or more leads 111a-d as is also known in the art. Various sets of parameters may define the pulse characteristics and pulse timing for the pulses applied to the various electrodes 111a-d as is known in the art. Although constant excitation pulse generating circuitry is contemplated for some embodiments, any other suitable type of pulse generating circuitry may be employed such as constant voltage pulse generating circuitry.

The sensing circuitry 158 may measure an electric potential (e.g., voltage, current) of proximate tissue through at least one of the electrodes 111a-d. The electric potential (EP) measurements may correspond to the EP signal generated by the target nerve fibers in response to the non-paresthesia stimulation waveform emitted from the electrodes 111a-d. The EP signal may be measured continuously corresponding to a collection window and recorded on the memory 161. The sensing circuitry 158 may measure a morphology or characteristics of the EP based on the electrical potential such as amplitude, latency, peak-to-peak amplitude, duration of one or more peaks, latency, and/or the like. The latency may correspond to an amount of time between delivery of the non-paresthesia stimulation waveform to the target nerve fiber and measurement of the EP. The sensing circuitry 158 may include amplifiers, filters, analog to digital converters, memory storage devices (e.g., RAM, ROM), digital signal processor, and/or the like.

The controller 151 may include a microcontroller, a microprocessor, and/or one or more processors executing programmed instructions for controlling the various components of the NS system 100. Software or firmware code may be stored in the memory 161 of the IPG 150 or integrated with the controller 151. Additionally or alternatively, the controller 151 may include an ASIC, a programmable logic device, one or more differential amplifiers (e.g., comparators), and/or the like dedicated hardware components for performing one or more operations described herein.

In various embodiments, the controller 151 and/or sensing circuitry 158 may analyze the morphology or characteristics of the EP signal measured by the sensing circuitry 158. One or more of the EP signal characteristics may change due to alteration in the type or extent of neurons activated by the non-paresthesia stimulation waveform, which may occur due to changes in patient posture (e.g., with dorsal-ventral movement of the lead 110 with respect to a spinal cord of the patient), migration of the lead 110, encapsulation of the lead 110 due to a foreign body response, or other changes to the NS system 100 or physiological response to the non-paresthesia stimulation waveform. Based on the EP signal compared to a predetermined threshold corresponding to a target EP signal, the controller 151 may automatically adjust the non-paresthesia stimulation waveform to approximately achieve the target EP signal.

For example, the controller 151 may execute a proportional integral derivative (PID) algorithm, which may determine an error rate or difference between the EP signal characteristic(s) and the predetermined threshold. The controller 151 based on the PID may adjust the non-paresthesia stimulation waveform to reduce the difference or error rate between the one or more characteristics of the EP signal.

Additionally or alternatively, the controller 151 may include a series of comparators, each corresponding to a different voltage potential threshold. For example, a first comparator may measure when the EP signal is at or above the EP signal target (e.g., output a high output or logic one), such as an amplitude of the EP signal. If the EP signal is below the EP signal target, the controller 151 may adjust the non-paresthesia stimulation waveform accordingly, such as increasing the amplitude or pulse width, based on the comparator measurements to increase the EP signal to reach the EP signal target. The controller 151 may further include a second comparator, which may measure when the EP signal is above an over stimulation threshold. If the second comparator is activated, the controller 151 may adjust the non-paresthesia stimulation waveform accordingly, such as decreasing the amplitude or pulse width, based on the second comparator measurements to decrease the EP signal.

An external device 160 may be implemented to charge/recharge the battery 154 of the IPG 150 (although a separate recharging device could alternatively be employed), to access the memory 161, and to program the IPG 150 on the pulse specifications and EP recording settings while implanted within the patient. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

Although, in alternative embodiments separate programmer devices may be employed for charging and/or programming the NS system 100. The external device 160 may be a processor-based system that possesses wireless communication capabilities. Software may be stored within a non-transitory memory of the external device 160, which may be executed by the processor to control the various operations of the external device 160.

Optionally, a "wand" 165 may be electrically connected to the external device 160 through suitable electrical connectors (not shown). The electrical connectors may be electrically connected to a telemetry component 166 (e.g., inductor coil) at the distal end of wand 165 through respective wires (not shown) allowing bi-directional communication with the IPG 150. The user may initiate communication with the IPG 150 by placing the wand 165 proximate to the NS system 100. Preferably, the placement of the wand 165 allows the telemetry system of the wand 165 to be aligned with the far-field and/or near field communication circuitry 155 of the IPG 150.

Additionally or alternatively, the external device 160 may include an RF transceiver to communicate to the IPG 150 using a wireless protocol such as Bluetooth, Bluetooth low energy, WiFi, MICS, and/or the like. For example, the far-field and/or near field communication circuitry 155 may include an RF transceiver.

The external device 160 preferably provides one or more user interfaces 168 (e.g., display, touch screen, keyboard, mouse, buttons, or the like) allowing the user to operate the IPG 150. The external device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different electrode 111*a-d* combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. Optionally, the user interface 168 may permit the user to designate which electrodes 111*a-d* are to stimulate (e.g., emit excitation pulses, in an anode state, in a cathode state) the stimulation target, to measure the evoked potential (e.g., connecting to the sensing circuitry 158) resulting from the excitation pulses, remain inactive (e.g., floating), or the like. Additionally or alternatively, the external device 160 may access or download the electrical measurements from the memory 161 acquired by the sensing circuitry 158.

Also, the external device 160 may permit operation of the IPG 150 according to one or more spinal cord stimulation (SCS) programs or therapies to treat the patient. For example, the SCS program corresponds to the SCS delivered and/or executed by the IPG 150. Each SCS program may include one or more sets of stimulation parameters (e.g., stimulation level) of the bursts including pulse amplitude, pulse width, pulse frequency or inter-pulse period, pulse repetition parameter (e.g., number of times for a given pulse to be repeated for respective stimset during execution of program), number of pulses within the burst, pulse shape, etc. forming the non-paresthesia stimulation waveform. The IPG 150 may modify its internal parameters in response to the control signals from the external device 160 to vary the characteristics of the non-paresthesia stimulation waveform emitted through the lead 110 to the target nerve fibers of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 2A:
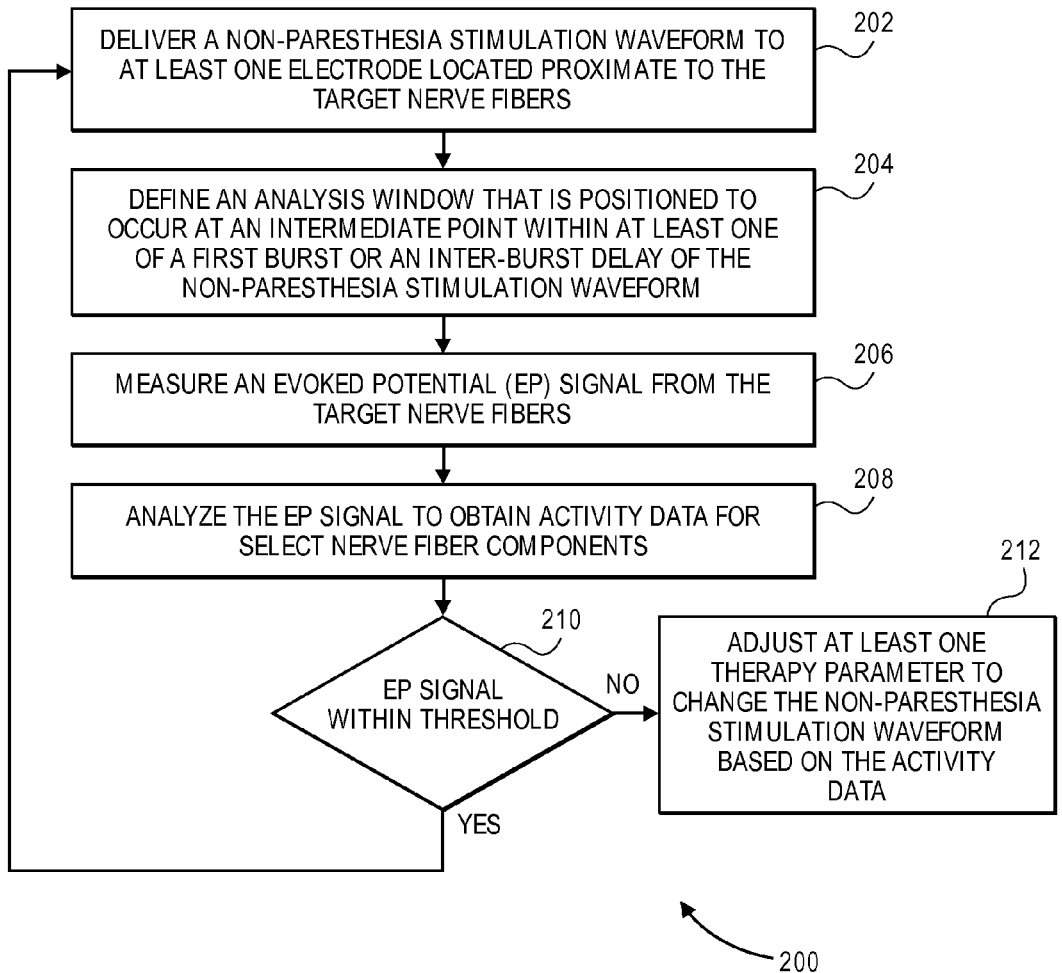
FIG. 2A is a flowchart of a method for closed loop spinal cord stimulation, according to an embodiment of the present disclosure.

FIG. 2A is a flowchart of a method 200 to control non-paresthesia stimulation of nerve tissue of a patient. The method 200 may employ structures or aspects of various embodiments (e.g., systems and/or methods) discussed herein. Optionally, the operations of the method 200 may represent actions to be performed by one or more circuits (e.g., the controller 151) that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the one or more processors. For example, the operations of the method 200 may represent actions of or performed by one or more processors when executing programmed instructions stored on a tangible and non-transitory computer readable medium.

In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It should be noted, other methods may be used, in accordance with embodiments herein.

One or more methods may (i) deliver a non-paresthesia stimulation waveform to at least one electrode located proximate to target nerve fibers, (ii) define an analysis window that is positioned to occur at an intermediate point within at least one of a first burst or an inter-burst delay, (iii) during the analysis window, measure evoked potential (EP) signals from the target nerve fibers, (iv) analyze the EP signals to obtain activity data for select nerve fiber components, and (v) adjust at least one therapy parameter to change the non-paresthesia stimulation waveform based on the activity data.

Beginning at 202, the implantable pulse generator 150 delivers a non-paresthesia stimulation waveform to at least one electrode located proximate to target nerve fibers. In connection with FIG. 3, a position of the at least one electrode may correspond to a placement of a lead 310.

Figure 3:
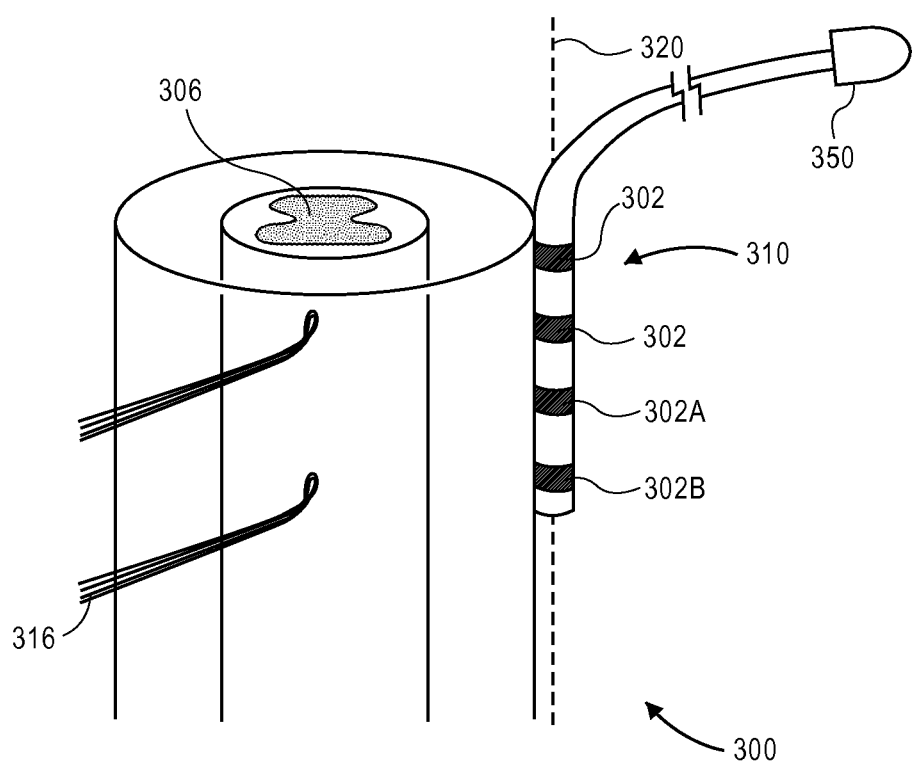
FIG. 3 illustrates a lead placement of a neurostimulation system, according to an embodiment of the present disclosure.

FIG. 3 is an illustration of a lead placement 300, in accordance with an embodiment. The lead 310 may extend parallel to a dorsal column (DC) 306 along an axis 320. The lead 310 may be positioned at a target position within an epidural space of the patient so as to be in close proximity to the DC 306. The lead 310 may include a plurality of electrodes 302 overlaid on the surface of the lead 310. The electrodes 302 may be electrically coupled to an IPG 350. The IPG 350 may be similar to and/or the same as the IPG 150.

The electrodes 302 may be proximate and/or adjacent to a dura layer 316 of the DC 306 allowing the electrodes 302 to stimulate at least a portion of the DC 306. The targeted location within the DC 306 may include afferent or sensory nerve fibers, such as Aβ sensory fibers, Aδ sensory fibers, C sensory fibers, and/or interneurons.

Additionally, the position of the electrodes 302 of the lead 310 enable one or more of the electrodes 302 (e.g., the electrodes 302a-b) to detect and/or measure the evoked potentials (EP) generated by the corresponding target nerve fiber such as the Aλ sensory, Aδ sensory, C sensory fibers, and/or interneurons in response to the non-paresthesia stimulation waveform emitted from the electrodes 302 (e.g., the electrode 302a). It should be noted in various embodiments, one or more of the electrodes 302 may be used for the non-paresthesia stimulation and measurement of the EP generated by the corresponding target nerve fibers. For example, the electrode 302a may emit the non-paresthesia stimulation and measure the EP generated by the corresponding target nerve fiber. Additionally or alternatively, a subset of the electrodes 302 may be used for emitting the non-paresthesia stimulation and another subset of the electrodes may be used to measure the EP generated by the corresponding target nerve fibers. For example, the electrode 302b may only emit the non-paresthesia stimulation.

The electrodes 302 are electrically coupled to the sensing circuitry of the IPG 350, which allow the IPG 350 to identify whether the target nerve fiber is affected by the non-paresthesia stimulation waveform. The electrodes 302 may enable the lead 310 to have a multi-contact array of multiple electrode pairs to detect propagation of the EPs generated by the corresponding target nerve fiber in response to pulses of the non-paresthesia stimulation waveform.

Figure 4:
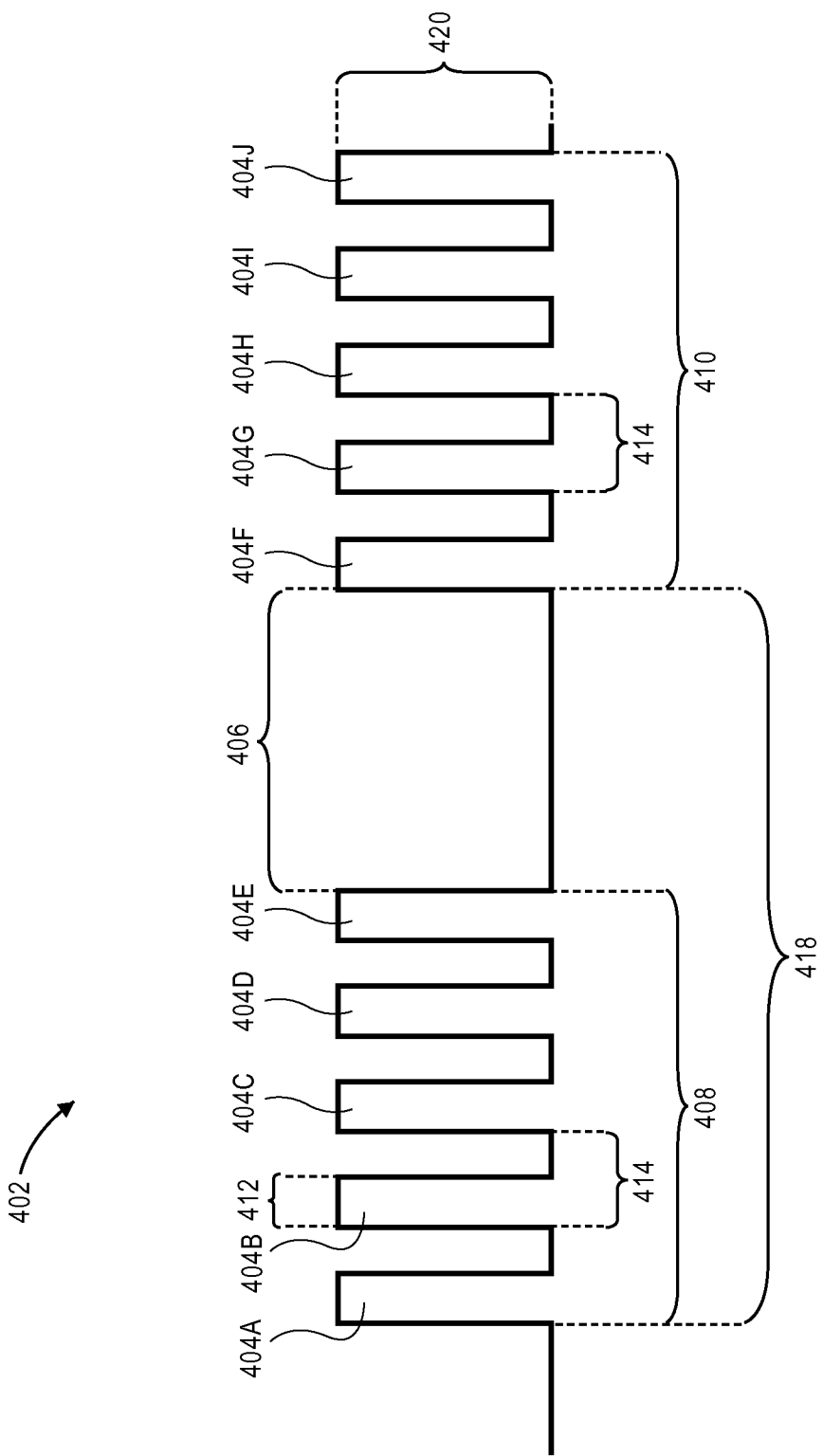
FIG. 4 illustrates a graphical representation of a non-paresthesia stimulation waveform, according to an embodiment of the present disclosure.

The non-paresthesia stimulation waveform, such as the non-paresthesia stimulation waveform 402 shown in FIG. 4, may be delivered by the IPG 350 to the at least one of the electrodes 302 (e.g., the electrode 302a), which is emitted by at least one of the electrodes 302. For example, pulses 404a-j of the non-paresthesia stimulation waveform may be delivered by the IPG 350 to the electrode 302a. The excitation pulses are emitted from the electrode 302a in an outward direction towards the targeted location within the DC 306 (e.g., the corresponding target nerve fiber). The non-paresthesia stimulation waveform 402 may be repeatedly emitted by the electrode 302a based on the SCS program.

FIG. 4 is a graphical representation of the non-paresthesia stimulation waveform 402. The non-paresthesia stimulation waveform 402 includes the pulses 404a-j having an amplitude 420 and a length corresponding to a pulse width 412. For example, the pulse width 412 may be 250 microseconds. It should be noted that the pulse width 412 may be longer that 250 microseconds, for example ranging from 250-2000 microseconds. The pulses 404a-j when emitted from at least one of the electrodes 302 excite at least a portion of the corresponding target nerve fibers, which enter a refractory state after being excited.

The pulses 404a-j are arranged in at least a first burst 408 and a second burst 410 separated by an inter-pulse delay 406. The first burst 408 and the second burst 410 correspond to a series of pulses 404a-j spaced at a select intra-burst pulse frequency 414 within the first burst 408 and the second burst 410. The intra-burst pulse frequency 414 may define when a successive pulse 404a-j occurs within the first burst 408 and/or second burst 410.

For example, the select intra-burst pulse frequency 414 may be 250 Hz, which corresponds to pulses 404a-j occurring within the first burst 408 and/or second burst 410 every 2 ms. It should be noted that the intra-burst pulse frequency 414 may be higher than 250 Hz, for example ranging from 250-1000 Hz. Additionally or alternatively, the intra-burst pulse frequency 414 may be less than 250 Hz.

Based on the intra-burst frequency 414, the pulses 404a-j may be arranged in the first burst 408 and/or in the second burst 410 to create a non-coherent neuronal activity pattern generated from the corresponding target nerve fibers. The non-coherent neuronal activity pattern may result from portions of the corresponding target nerve fibers entering refractory states after being "excited" by the pulses 404a-j at different times within the first burst 408 and/or second burst 410. For example, a first pulse 404a and a successive pulse, a second pulses 404b, may be timed within the first burst 408 such that the second pulse 404b is delivered during a neuronal refractory period following the first pulse 404a, such that only a subpopulation of neurons that have recovered from the refractory state will fire an action potential in response to the second pulse 404b.

The spacing between the pulses 404, which corresponds to the intra-burst frequency 414, may be configured such that successive pulses 404a-j occur when at least a portion of the neurons within the corresponding target nerve fibers may be excited. For example, the intra-burst pulse frequency 414 may be configured such that a first pulse 404a, a second pulse 404b, and a third pulse 404c are timed such that over a course of the first burst 408, different neurons within a population of the target nerve fiber are excited at different times, and thereby show a lack of coherence.

It should be noted that although the first burst 408 and the second burst 410 are each shown having five pulses 404, in other embodiments the first burst 408 and the second burst 410 may have more than five pulses 404a-j or less than five pulses 404. Additionally or alternatively, the first burst 408 and the second burst 410 may have a different number of pulses 404, respectively. For example, the first burst 408 may have more pulses 404a-j or less pulses 404a-j than the second burst 410.

The first burst 408 and the second burst 410 may be spaced at a select inter-burst frequency 418. The inter-burst pulse frequency 418 may define when successive bursts, e.g., the second burst 410 relative to the first burst 408, occurs within the non-paresthesia waveform 402. For example, the select inter-burst pulse frequency 418 may be 20 Hz. It should be noted that the inter-burst pulse frequency 418 may be higher than 20 Hz, for example ranging from 20-60 Hz. Additionally or alternatively, the inter-burst pulse frequency 418 may be less than 20 Hz.

The number of pulses 404a-j within the first burst and second bursts 408 and 410, the amplitude 420 and/or pulse width 412 of the pulses 404a-j, the inter-burst delay 406, the inter-burst pulse frequency 418, and/or the intra-burst frequency 414 may be based on a stimulation level of the non-paresthesia stimulation waveform 402. The stimulation levels may be defined by the SCS program stored on the memory 161 and/or executed by a controller of the IPG 350 (e.g., the controller 151). For example, the IPG 350 may be programmed or receive the SCS program from an external device (e.g., the external device 160).

Returning to FIG. 2A, at 204, an analysis window may be defined by the controller 151. For example, the IPG 350 may record or acquire data continuously or during select times during the non-paresthesia stimulation waveform 402 emitted from one or more of the electrodes 302. The analysis window may correspond to a length of time of interest during the non-paresthesia stimulation waveform 402, such as during an EP, within the collection window. For example, during the collection window the sensing circuitry 158 may measure an electrical potential (e.g., voltage) from at least one of the electrodes 302. The analysis window may be selected by the controller 151 within the collection window corresponding to measurements of the collection 151 of when an EP signal generated by a portion of the corresponding target nerve fiber is measured by the sensing circuitry 158. It should be noted in various embodiments a length of the analysis window may be smaller than the collection window (e.g., a portion of the collection window), and/or approximately equal to the collection window.

Figure 5:
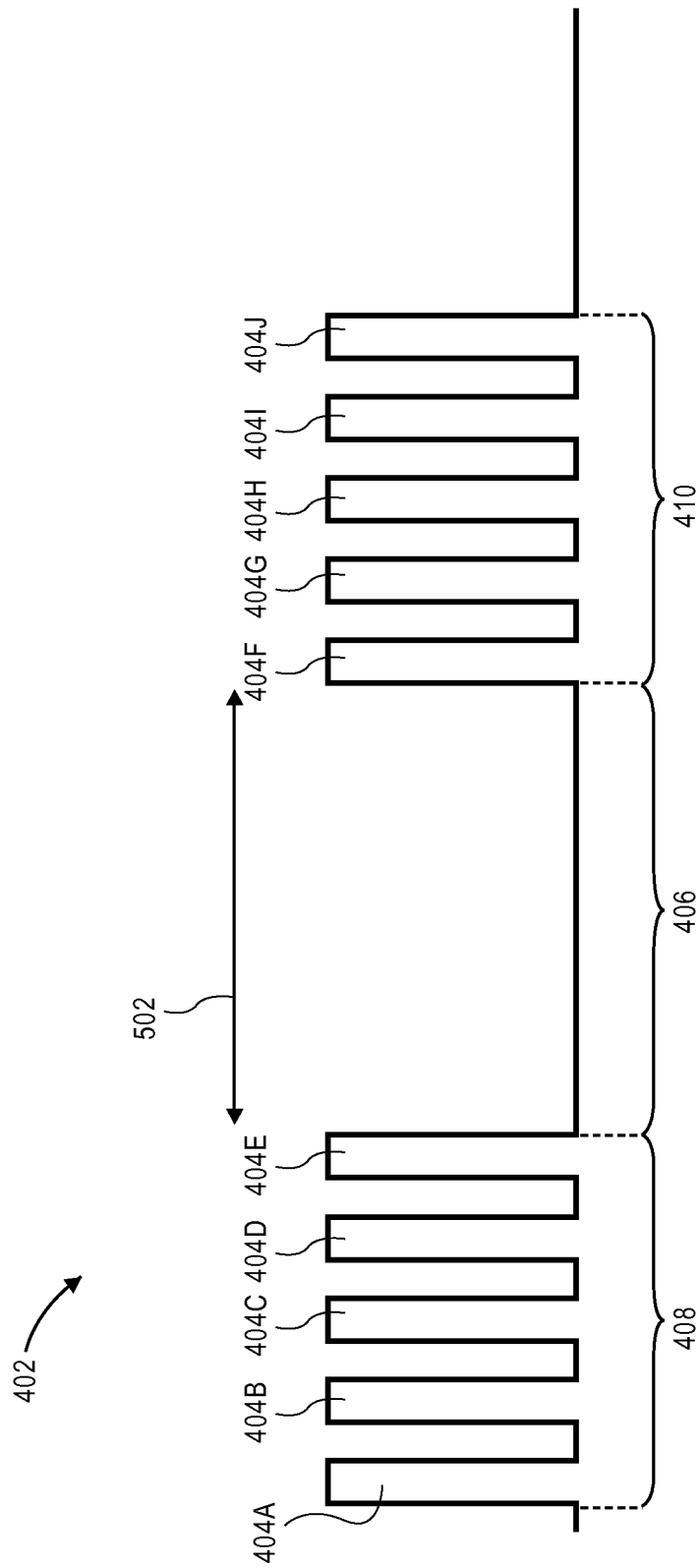
FIG. 5 illustrates an analysis window within an inter-burst delay, according to an embodiment of the present disclosure.
Figure 6:
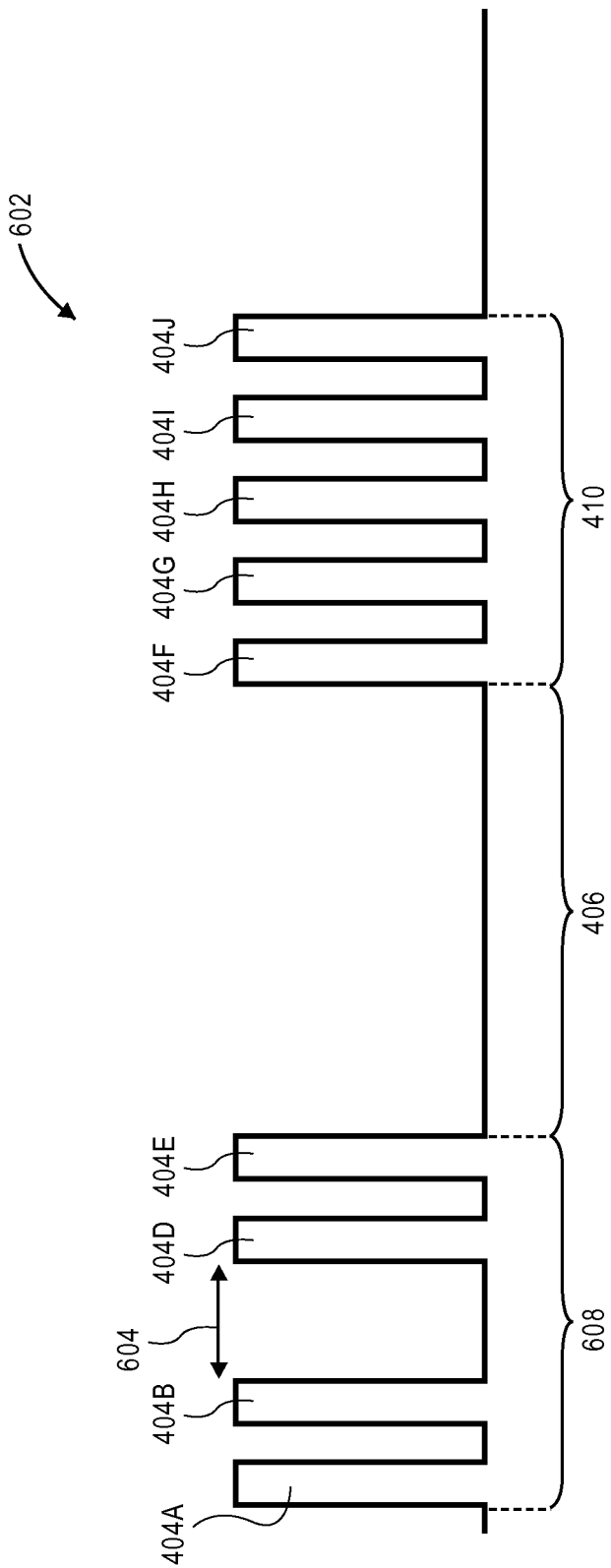
FIG. 6 illustrates an analysis window within a burst of a non-paresthesia stimulation waveform, according to an embodiment of the present disclosure.

The analysis window is positioned by the controller 151 with respect to the non-paresthesia stimulation waveform 402 to overlap at least a trailing portion of the refractory state induced by the associated preceding pulses. For example, the start of the analysis window w may be positioned within four milliseconds of one of the pulses 404. The EP measured during the analysis window at the electrodes 302 may correspond to the EP signal generated by a portion of the target nerve fibers when excited by the pulses 404a-j of the non-paresthesia stimulation waveform 402. The analysis window may be positioned to occur at an intermediate point within at least one of the first burst 408 or the inter-burst delay 406 of the non-paresthesia stimulation waveform 402. FIGS. 5-6 illustrate positions of the analysis window in accordance with embodiments described herein.

FIG. 5 illustrates an analysis window 502 positioned relative to the non-paresthesia stimulation waveform 402 of FIG. 4. The analysis window 502 is positioned after the first burst 408, and within the inter-burst delay 406. For example, the analysis window 502 may start after the pulse 404e of the first burst 408, and end prior to the pulse 404f of the second burst 410.

FIG. 6 illustrates an analysis window 604 positioned within a modified non-paresthesia stimulation waveform 602. The modified non-paresthesia stimulation waveform 602 includes a modified first burst 608, which is based on the first burst 408 of FIG. 4. For example, the controller 151 modifies or changes the non-paresthesia stimulation waveform 402 to include the analysis window 604. The modified first burst 608 includes pulses, such as the first pulse 404a and the last pulse 404e, similar to and/or the same as the first burst 408. The modified non-paresthesia stimulation waveform 602 is formed by the controller 151 suppressing one or more intermediate pulses (e.g., the pulse 404c in the first burst 408), and replacing the one or more intermediate pulses with the analysis window 604. For example, the controller 151 may not deliver the intermediate pulse, the pulse 404c, to one or more of the electrodes 302, suppressing or omitting the intermediate pulse from the modified non-paresthesia stimulation waveform 602.

The intermediate pulses correspond to pulses positioned within a bursts, such as the pulses 404b-d or the pulses 404g-i, between the first pulse (e.g., the pulse 404a, the pulse 404f) and the last pulse (e.g., the pulse 404e, the pulse 404j) of the burst. For example, the analysis window 604 is positioned within the modified first burst 608 such that the EP signals are measured at an intermediate point within the modified first burst 608 that is after the first pulse 404a and before the last pulse 404e. It should be noted in various other embodiments, the last pulse of the burst (e.g., the pulse 404e, the pulse 404j) may be suppressed to include the analysis window 604. Additionally or alternatively, multiple pulses (e.g., adjacent pulses) may be suppressed to include the analysis window 604.

The analysis window 604 may extend from a termination of the preceding pulse 404b to a starting location of the subsequent pulse 404d. For example, the analysis window 604 may be four milliseconds in length. It should be noted in other embodiments the analysis window 604 may be less than four milliseconds (e.g., two milliseconds) or greater than four milliseconds (e.g., ranging from four milliseconds to eight milliseconds). Alternatively, a length the analysis window 604 may be based on the frequency of the modified non-paresthesia stimulation waveform 602 corresponding to an amount of time between pulses 404b-404d. For example, a collection window may be larger for modified non-paresthesia stimulation waveforms with a lower intra-burst frequency relative to higher intra-burst frequencies. In another example, intra-burst frequency may be 500 hertz resulting in the pulse 404d occurring approximately three milliseconds after the preceding pulse 404b. Thereby, a length of the analysis window 604 will be less than and/or approximately the same as three milliseconds.

The analysis window 604 is positioned by the controller 151 to overlap at least a trailing portion of the refractory state induced by the associated preceding pulses. For example, the analysis window 604 is positioned subsequent to the pulse 404b. The pulse 404b may excite at least a portion of the corresponding target nerve fibers, which enter a refractory state after being excited. The analysis window 604 is positioned proximate to the pulse 404b to acquire EP during at least a trailing portion of the refractory state of the excited target nerve fibers, which correspond to EP signal measurements. For example, the duration of the refractory state of the corresponding target nerve fibers may vary from one to four milliseconds after being excited by the pulse 404b. The start of the analysis window 604 may be positioned within four milliseconds of the pulse 404b within the first burst 608 to have the analysis window 604 overlap at least a trailing portion of the refractory state of the corresponding target nerve fibers.

Figure 7:
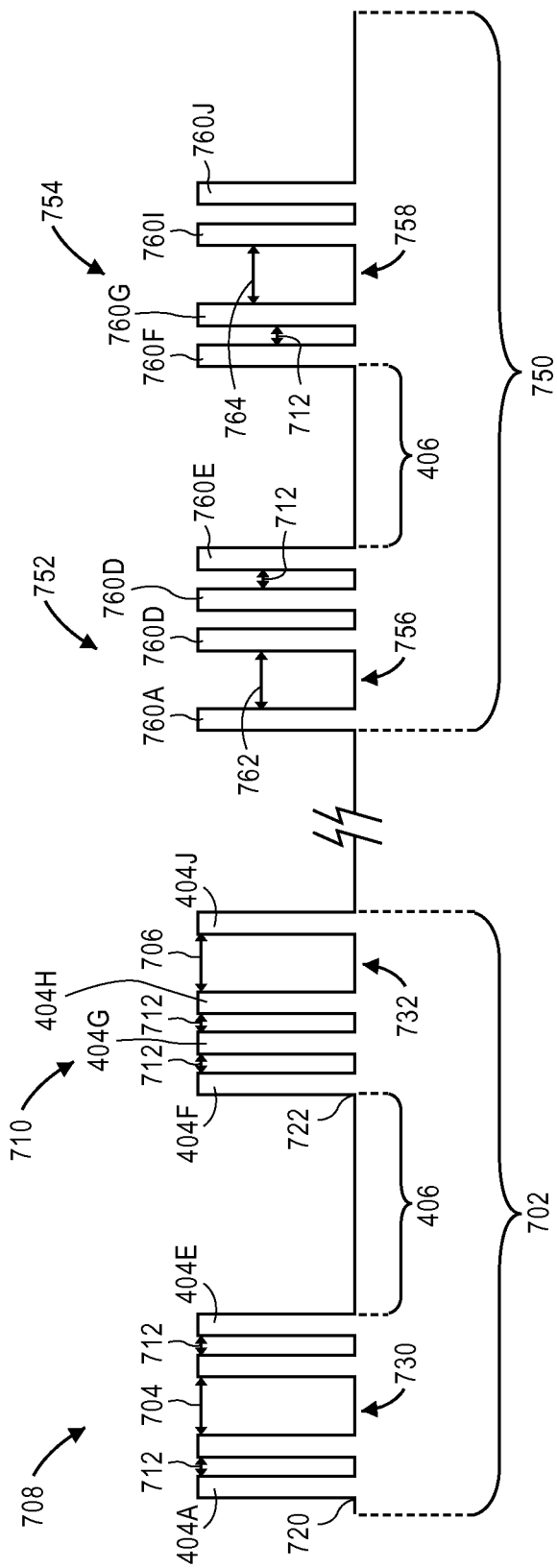
FIG. 7 illustrates analysis windows of modified non-paresthesia stimulation waveforms, according to an embodiment of the present disclosure.

Additionally or alternatively, in connection with FIG. 7, the controller 151 may modify the non-paresthesia stimulation waveform 402 by suppressing intermediate pulses (e.g., the pulses 404b-404d, the pulses 404g-404i) within the first burst 408 and/or the second burst 410 with a first and second collection window, respectively.

FIG. 7 illustrates a first analysis window 704 and a second analysis window 706 positioned within a modified non-paresthesia stimulation waveform 702. The analysis windows 704 and 706 being within the first and second bursts 708 and 710, respectively, provide EP signal measurements corresponding to neural activity at different times relative to start points 720 and 722 of each the first burst 708 and second burst 710.

The modified non-paresthesia stimulation waveform 702 includes a modified first burst 708 and second burst 710 based on the first burst 408 and second burst 410, respectively, of the non-paresthesia stimulation waveform of FIG. 4. The first burst 708 and the second burst 710 illustrated in FIG. 7 include at least four pulses each, 404a-e and 404f-j separated by inter-pulse delays 712. It should be noted in other embodiments the first burst 708 and the second burst 710 may have more or less than four pulses each 404a-e and 404f-j.

The inter-pulse delays 712 may correspond to an intra-burst pulse frequency defining when a successive pulse 404a-j occurs within the first burst 708 and/or the second burst 710. The first burst 708 may extend from a starting point 720 ending at the pulse 404e, which corresponds to a start of the inter-burst delay 406. The second burst 710 may extend from a starting point 722, which correspond to an end of the inter-burst delay 406, and ending at the pulse 404j.

The controller 151 may suppress a pulse of the non-paresthesia stimulation waveform 402 (e.g., the pulse 404c of FIG. 4) at the first location 730 and suppress a pulse (e.g., the pulse 404i) at the second location 732 at the first burst 708 and the second burst 710. It should be noted in various other embodiments, the controller 151 may suppress more than one pulse of the non-paresthesia stimulation waveform 402.

The controller 151 may replace the suppressed pulses at the first and second locations 730, 732 with the analysis windows 704 and 706, respectively. The analysis windows 704 and 706 may extend from pulse-to-pulse. Lengths of the analysis windows 704 and 706 may be based on the inter-pulse delays 712 and/or the pulse width 412 of the pulses 404a-j. For example, a length of the analysis window 704 may be at least four milliseconds extending from the ends of the previous and subsequent pulses 404, relative to the suppressed pulse, corresponding to a length of the pulse width 412 of the suppressed pulse and the two inter-pulse delays 712. It should be noted in other embodiments the analysis windows 704 and 706 may be less than or greater than four milliseconds, for example, ranging from four to eight milliseconds.

The analysis windows 704 and 706 are positioned by the controller 151 to overlap at least a trailing portion of the refractory state induced by the associated preceding pulses 404a-b and 404f-g, respectively.

Additionally, the analysis windows 704 and 706 are positioned at different times of the first burst 708 and the second burst 710 relative to the starting points 720 and 722. The different times of the analysis windows 704 and 706 relative to the starting positions 720 and 722 allow the sensing circuitry of the IPG 350 to acquire EP signal measurements from target nerve fibers excited by a different number of pulses 404a-j. For example, the morphology of the EP signal depends on neuronal coherence during the first and second bursts 708 and 710. The number of pulses 404a-j may be based on the position of the communication window 704, 706 with respect to the starting position 720, 722 of the corresponding burst 708, 710.

For example, the communication window 704 is positioned at the first location 730, and is positioned at a mid-point of the first burst 708, interposed between the pulses 404a-b and the pulses 404d-e. Based on the position of the communication window 704, the sensing circuitry may acquire EP signal measurements from the corresponding target nerve fibers excited by two pulses, the pulses 404a-b. The communication window 706 is positioned at the second location 732, and is positioned off-set within the second burst 710 by having an additional pulse between the communication window 706 and the starting position 722 relative to the last pulse 404j of the second burst 710. Based on the position of the communication window 706, the sensing circuitry may acquire EP signal measurements from the corresponding target nerve fibers excited by the pulses 404f-404h.

Optionally, the controller 151 may shift a location of multiple analysis windows within a series of bursts following the first and second bursts 708 and 710. For example, in connection to a second modified non-paresthesia stimulation waveform 750, the controller 151 may alter the location of the analysis windows of the subsequent bursts between by suppressing intermediate pulses between a first and last pulse of the corresponding burst.

The second modified non-paresthesia stimulation waveform 750 may be delivered by the controller 151 subsequent to the modified non-paresthesia stimulation waveform 702. It should be noted that the second modified non-paresthesia stimulation waveform 750 may be delivered by the controller successively after the modified non-paresthesia stimulation waveform 702. Optionally, one or more non-paresthesia stimulation waveforms 402 may be delivered by the controller 151 interposed between the modified non-paresthesia stimulation waveform 702 and the second modified non-paresthesia stimulation waveform 750.

The second modified non-paresthesia stimulation waveform 750 includes a third burst 752 and a fourth burst 754 with corresponding analysis windows 762 and 764. Similar to the first and second bursts 708 and 710, the third burst 752 and the fourth burst 754 may include at least four pulses each 760a-j separated by inter-pulse delays 712. The pulses 760a-j may have electrical specifications (e.g., pulse width, amplitude) similar to and/or the same as the pulses 404a-j.

The third burst 752 and the fourth burst 758 have third and fourth locations 756 and 758, respectively, corresponding to suppressed pulses. Positions of the third and fourth locations 756 and 758 may be selected by the controller 151 based on positions of the communication window of the preceding burst. For example, the controller 151 may select a different location for the communication window such that the location of the communication window corresponding to the preceding burst is different.

Figure 8:
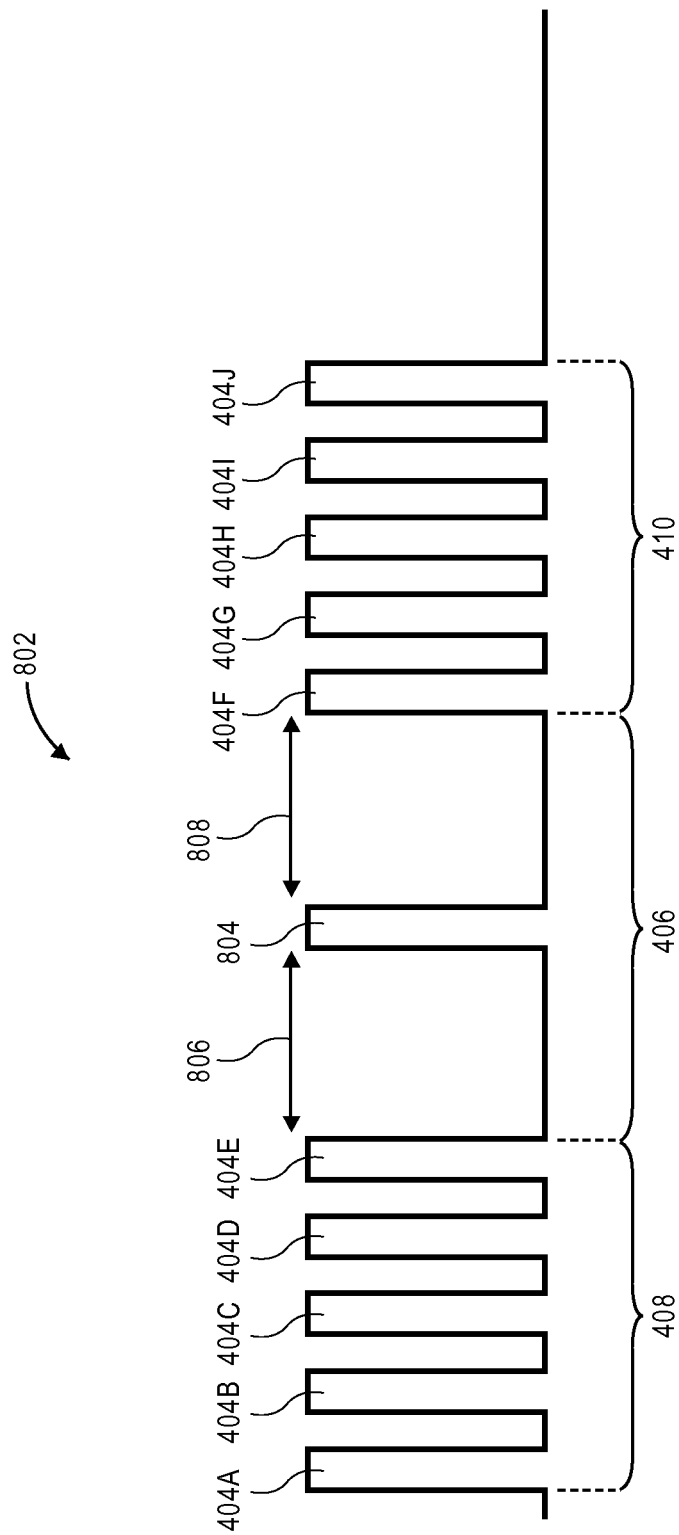
FIG. 8 illustrates a modified non-paresthesia stimulation waveforms that includes a test pulse, according to an embodiment of the present disclosure.

Additionally or alternatively in connection with FIG. 8, the controller 151 may define an analysis window 808 after a test pulse 804 and before the second burst 410.

FIG. 8 illustrates a modified non-paresthesia stimulation waveform 802. The modified non-paresthesia stimulation waveform 802 includes the test pulse 804 delivered during the inter-pulse delay 406 based on the non-paresthesia stimulation waveform 402 of FIG. 4. For example, the controller 151 may modify or change the non-paresthesia stimulation waveform 402 of FIG. 4 by delivering the test pulse 804 during the inter-pulse delay 406. The test pulse 804 is separate and distinct from the first and second bursts 408 and 410. The test pulse 804 may be delivered after a test pulse delay 806 from the last pulse 404e of the first burst 408. The test pulse delay 806 may be based on a refractory period of the corresponding target nerve fibers. For example, the test pulse delay 806 may be greater than one millisecond.

The analysis window 808 is positioned between the test pulse 804 and the first pulse 404f of the second burst 410. The length of the analysis window 808 may be configured to have a longer duration than the duration of an evoked response from the corresponding target nerve fibers excited by the test pulse 804. For example, the analysis window 808 may be three milliseconds. It should be noted in other embodiments the analysis window 808 may be less than or greater than three milliseconds, for example, four milliseconds.

Additionally or alternatively, the test pulse delay 806 may be adjusted for subsequent inter-pulse delays. For example, in connection with FIG. 9, the controller 151 may deliver a series of bursts with test pulses (e.g., the test pulses 804, 920, 922) delivered during select inter-burst delays 406 and shifting a position of the test pulses and corresponding analysis windows (e.g., analysis windows 808, 908, 912) relative to an end of preceding bursts.

Figure 9:
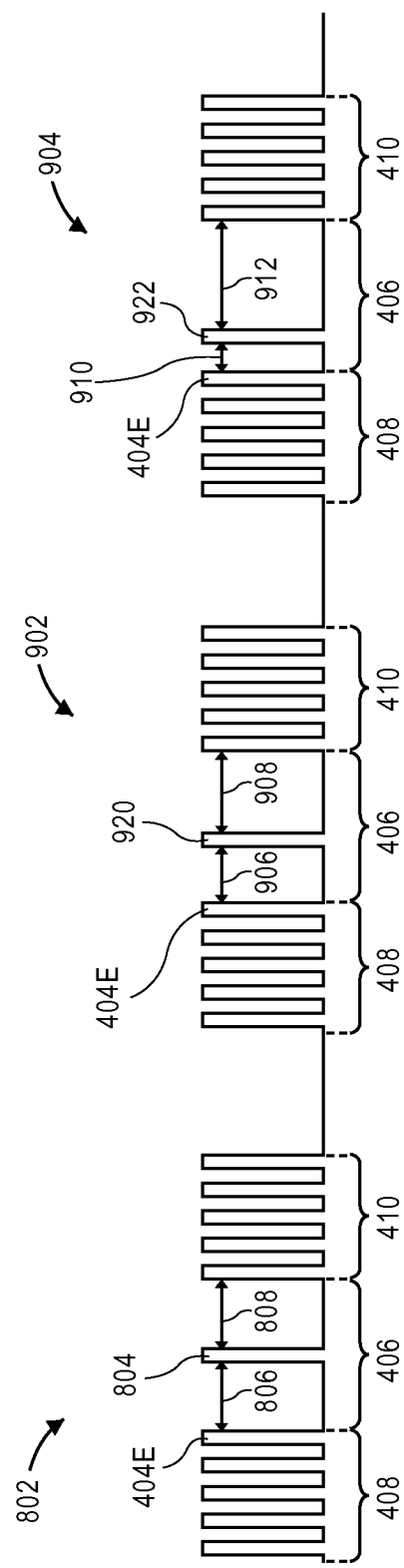
FIG. 9 illustrates modified non-paresthesia stimulation waveforms that include test pulses, according to an embodiment of the present disclosure.

FIG. 9 illustrates modified non-paresthesia stimulation waveforms 802, 902, and 904. Each of the non-paresthesia stimulation waveforms 802, 902, and 904 include a corresponding test pulse 804, 920, and 922. The test pulses 920 and 922 may have electrical specifications (e.g., pulse width, amplitude) similar to and/or the same as the test pulse 804. The test pulses 804, 920 and 922 are delivered at different positions within the inter-burst delays 406 relative to each other. For example, the controller 151 may adjust the test pulse delays 906, and 910 for the non-paresthesia stimulation waveforms 902 and 904 relative to the test pulse delay 806. As illustrated in FIG. 9, the controller 151 may iteratively decrease a length of the test pulse delay 906, 910 relative to a preceding test pulse delay. For example, the length of the test pulse delay 906 is shorter than a length of the test pulse delay 806. Additionally, the length of the test pulse delay 910 is shorter than the lengths of the test pulse delays 806 and 906.

The adjustment in the test pulse delays 906 and 910 shift the positions of the test pulses 920 and 922 relative to the last pulses 404e of the first bursts 408. For example, the test pulses 804, 920, and 922 are delivered by the controller 151 after the test pulse delays 806, 906, and 910, respectively. Reducing the length of the test pulse delays 906 and 910 results in the test pulses 920 and 922 occurring earlier within the inter-burst delays 406 relative to the test pulse 804.

The controller 151 may further adjust a position of the analysis windows 908 and 912 based on the adjusted position of the test pulses 920 and 922. For example, the analysis windows 908 and 912 may occur earlier within the inter-burst delays 406 relative to the analysis window 808. Additionally or alternatively, the analysis windows 908 and/or 912 may be longer than the analysis window 808 based on the increased length of time between the test pulses 920 and 922 and the beginning of the second bursts 410.

It should be noted that the series of bursts shown in FIG. 9 illustrates a series of burst corresponding to successively modified non-paresthesia stimulation waveforms 902, and 904. Various embodiments may have series of bursts from the non-paresthesia stimulation waveform 402 interposed with or between the modified non-paresthesia stimulation waveforms 902, and 904.

Returning to FIG. 2A, at 206, an evoked potential (EP) signal is measured by the sensing circuitry 158 from the target nerve fibers. The EP signal may be generated in response to the first burst 408 and/or the modified first bursts 608, 708, or third burst 752. Additionally or alternatively, the EP signal may be generated in response to the test pulse 804, 920, and/or 922. It should be noted that in various other embodiments, the EP signal may be measured in response to the EP signal generated in response to the second burst 410 and/or modified second bursts.

Figure 10:
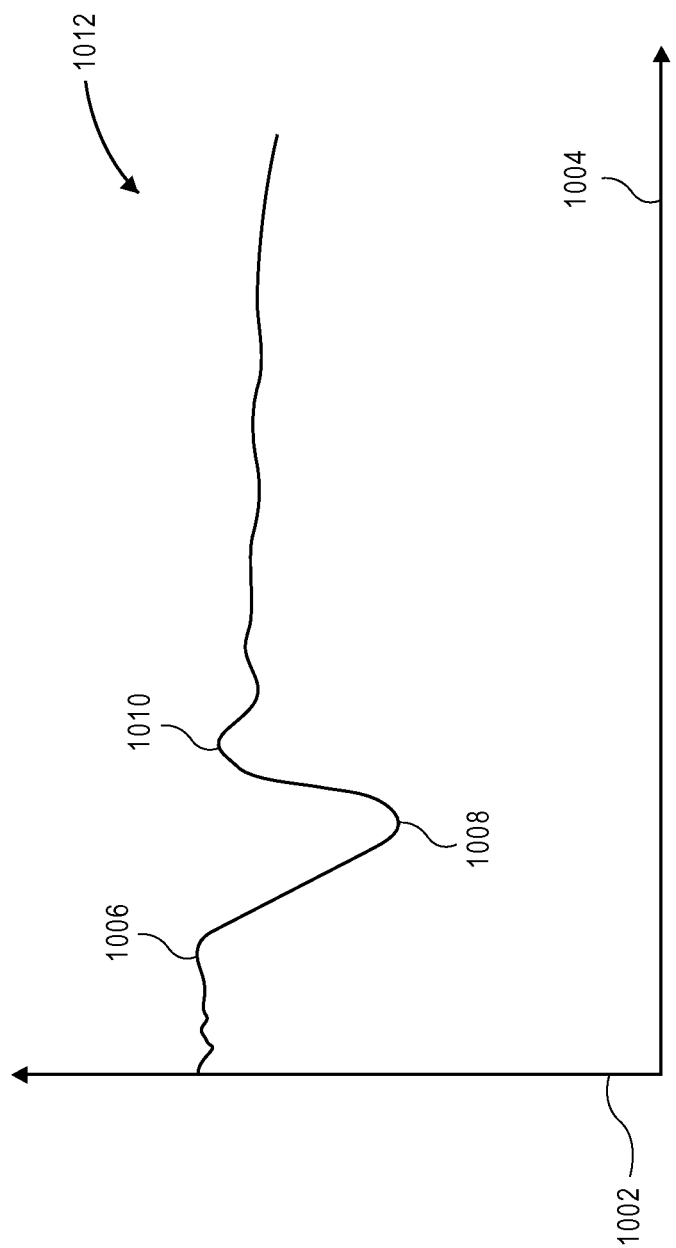
FIG. 10 illustrates an evoked potential signal measured during the analysis window of FIG. 5.

FIG. 10 illustrates a graphical representation of an EP signal 1012 measured by the sensing circuitry 158 during the analysis window 502 of FIG. 5. The EP signal 1012 was generated in response to the first burst 408. A horizontal axis 1004 represents time, and a vertical axis 1002 represents an electrical potential (e.g., voltage) of the sensed electrical potentials measured by the sensory circuitry 158 during the analysis window 502 from at least one of the electrodes 302. The electrical potential measurements form the EP signal 1012 resulting from the first burst 408.

The EP signal 1012 is a multiphasic evoked response generated from at least a portion of the target nerve fibers that were excited by one or more pulses 404a-e of the first burst 408. The EP signal 1012 is shown having a tri-phasic structure with a positive phase, a negative phase, and a secondary positive phase, which are represented as a first positive peak 1006, a negative peak 1008, and a secondary positive peak 1010 of the EP signal 1012.

Figure 11:
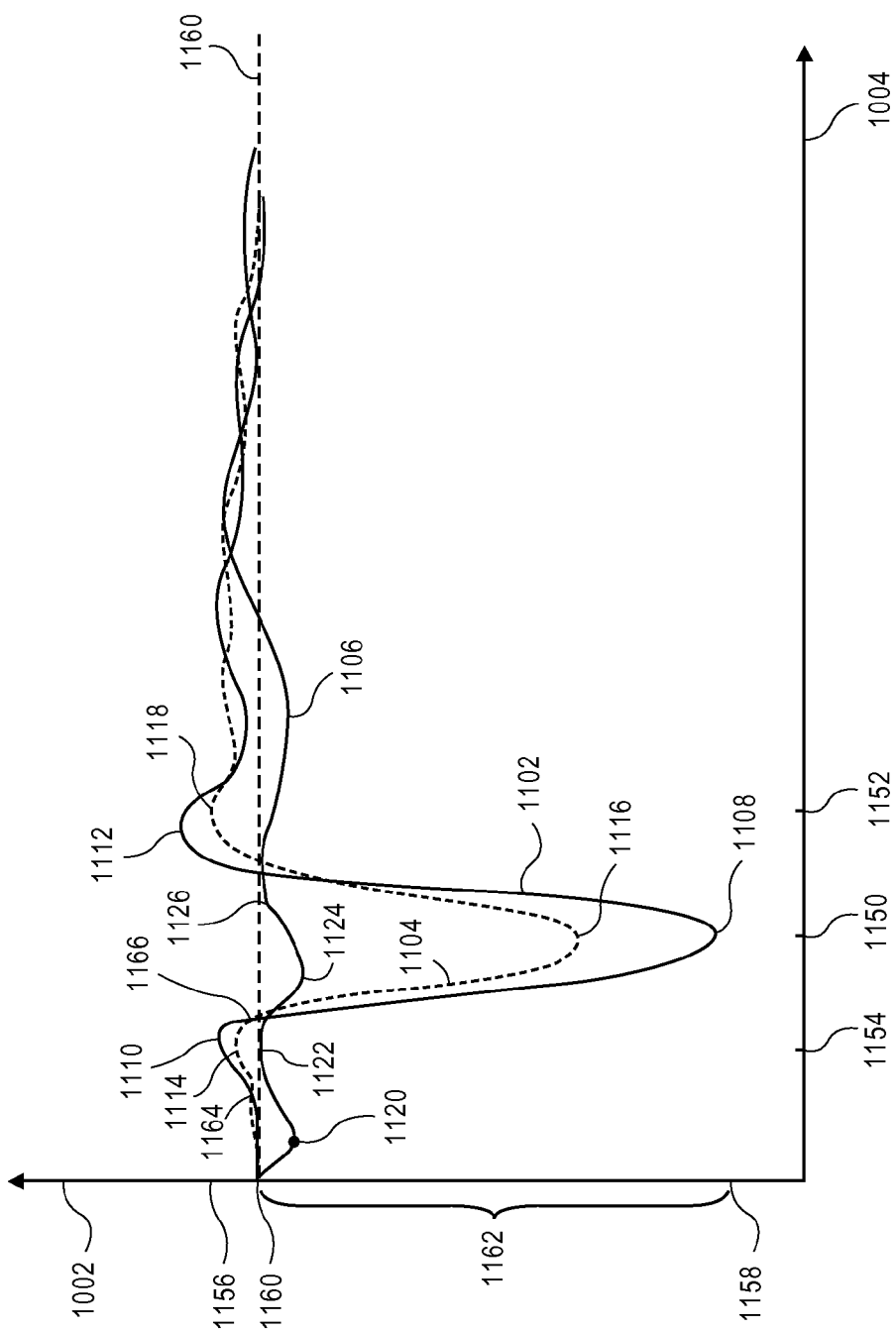
FIG. 11 illustrates evoked potential signals measured during the analysis window of FIG. 7.
Figure 12:
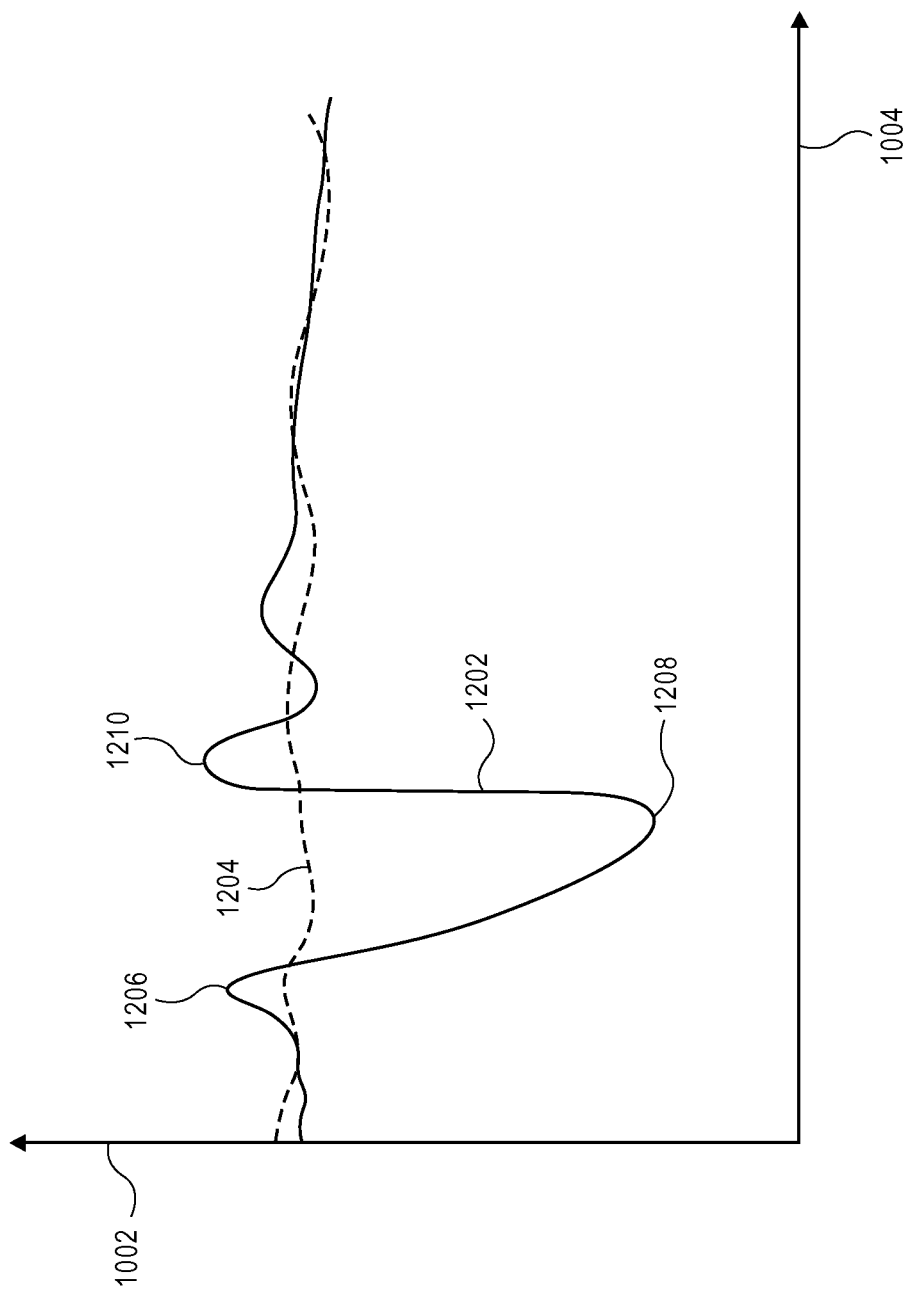
FIG. 12 illustrates evoked potential signals measured during analysis windows of the modified non-paresthesia stimulation waveforms of FIG. 9.

In connection with FIGS. 11 and 12, the structure of the EP signal measured by the sensing circuitry 158 may be affected by a position of the analysis window with respect to the modified non-paresthesia stimulation waveform 602, 702, 750, 802, 902, or 904.

FIG. 11 illustrates a graphical representation of EP signals 1102-1106 measured during the analysis windows 704, 706, and 762 of the modified non-paresthesia stimulation waveforms 702 and 750 shown in FIG. 7. The EP signal 1102 was measured by the sensing circuitry 158 during the analysis window 762. The EP signal 1104 was measured by the sensing circuitry 158 during the analysis window 704. The EP signal 1106 was measured by the sensing circuitry 158 during the analysis window 706.

The morphology or characteristics of the EP signals 1102-1106 may depend on the extent of neuronal coherence associated with a position of the analysis window 704, 706, and 762 within the corresponding bursts 708, 710, 752.

For example, the analysis window 762 is positioned after the first pulse 760a of the third burst 752. Since the target nerve fibers are being excited by the first pulse 760a, the largest portion of the target nerve fibers will not be in a refractory state, with respect to the remaining pulses 760b-760e of the third burst 752, and thereby excitable. The corresponding target nerve fibers excited by the first pulse 760a may generate the EP signal 1102 in response to the first pulse 760a, and is measured by the sensing circuitry 158. The EP signal 1102 includes a first positive peak 1110, a negative peak 1108, and a second positive peak 1112.

The analysis window 704 is positioned after the pulses 404a-b of the first burst 708. During the second pulse 404b a portion of the target nerve fibers may still be within a refractory state caused by the excitation of the preceding pulse, the first pulse 404a, of the first burst 708. Thereby, the portion of target nerve fibers excited by the second pulse 404b may be less than or a subset of the portion excited by the first pulse 404a.

The corresponding target nerve fibers excited by the second pulse 404b generate the EP signal 1104 in response to the second pulse 404b, and is measured by the sensing circuitry 158. The EP signal 1104 includes a first positive peak 1114, a negative peak 1116, and a second positive peak 1118. The reduced number of target nerve fibers excited by the second pulse 404b may alter characteristics (e.g., peak amplitude, latency, duration of positive/negative phases) of the EP signal 1104 relative to the EP signal 1102. For example, the peak-to-peak amplitude of the first positive peak 1114 to the negative peak 1116 is less than the peak-to-peak amplitude of the first positive peak 1110 to the negative peak 1108.

The analysis window 706 is positioned after the pulses 404*f-h* of the second burst 710. Similar to the second pulse 404*b* described in relation to the first burst 708, during the third pulse 404*h* a portion of the target nerve fibers may still be within a refractory state caused by the excitation of the preceding pulse, the first and second pulses 404*f-g*, of the second burst 708. Thereby, the portion of target nerve fibers excited by the third pulse 404*h* may be less than or a subset of the portion excited by the first pulse 404*f* and/or the second pulse 404*g*.

The corresponding target nerve fibers excited by the third pulse 404*h* generate the EP signal 1106 in response to the third pulse 404*h*, and is measured by the sensing circuitry 158. The reduced number of target nerve fibers excited by the third pulse 404*h* may alter characteristics (e.g., peak amplitude, latency, duration of positive/negative phases) of the EP signal 1106 relative to the EP signals 1102 and 1104. For example, the EP signal 1106 includes a plurality of peaks 1120-1126 having amplitudes less than the peaks (e.g., the first positive peak 1110, the negative peak 1108, the second positive peak 1112, the first positive peak 1114, the negative peak 1116, the second positive peak 1118) of the EP signals 1102 and 1104.

FIG. 12 illustrates a graphical representation of EP signals 1202 and 1204 measured during the analysis windows 808 and 912 of the modified non-paresthesia stimulation waveforms 802 and 904 shown in FIG. 9. The EP signal 1202 was measured by the sensing circuitry 158 during the analysis window 808. The EP signal 1202 includes a first positive peak 1206, a negative peak 1208, and a second positive peak 1210. The EP signal 1204 was measured by the sensing circuitry 158 during the analysis window 912.

Returning to FIG. 2A, at 208, the EP signal (e.g., the EP signal 1012, 1102-1106, 1202, 1204) is analyzed by the controller 151 to obtain activity data for select nerve fiber components. The select nerve fiber components may correspond to afferent or sensory nerve fibers, such as the Aβ sensory fibers, the Aδ sensory fibers, the C sensory fibers, and/or interneurons corresponding to the target nerve fibers. Based on characteristics or a morphology of the EP signal, the controller 151 may determine activation of one or more of the select nerve fiber components in response to the non-paresthesia stimulation waveform.

Figure 2B:
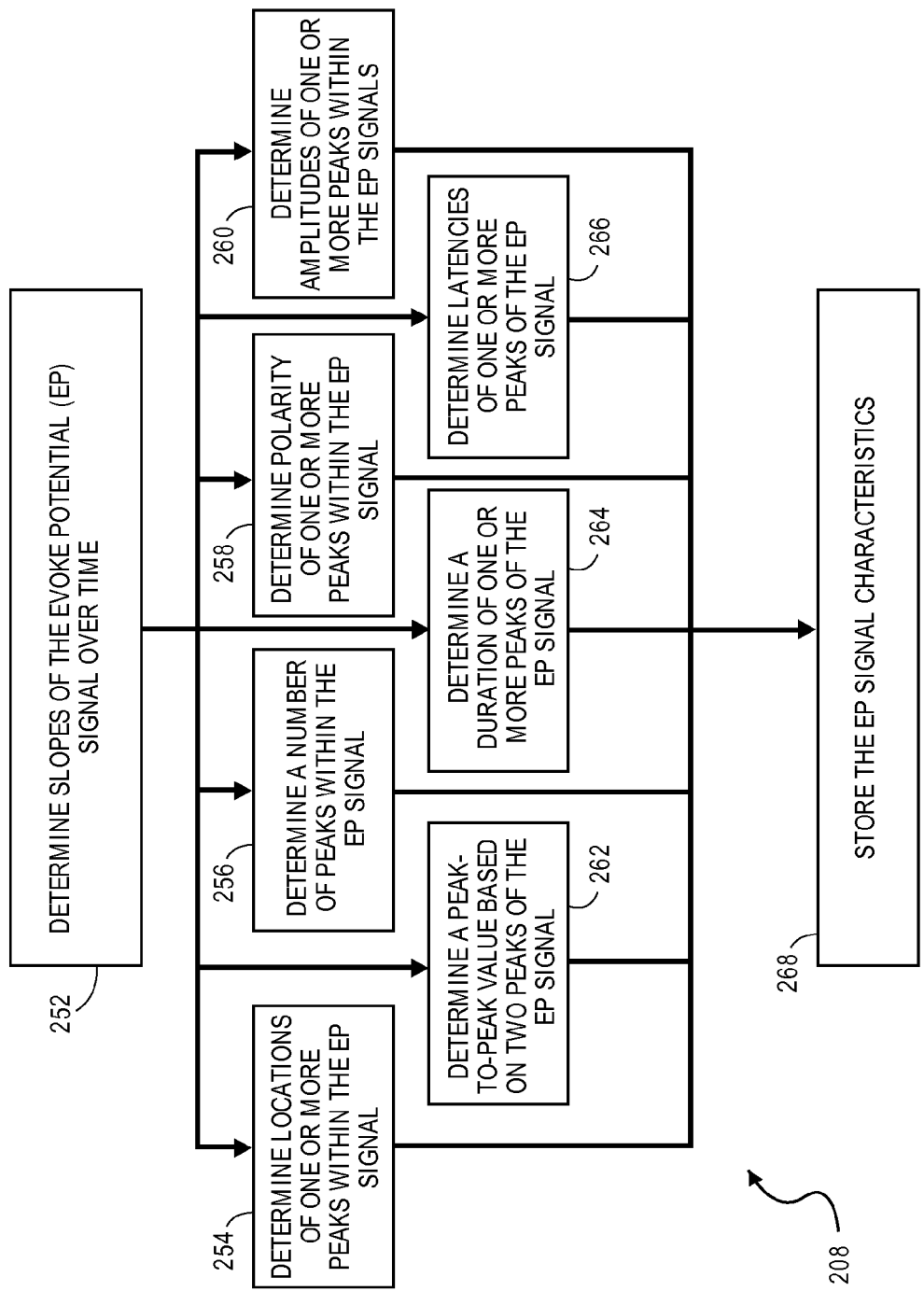
FIG. 2B is a flowchart of various operations to analyze an evoked potential signal, according to an embodiment of the present disclosure.

For example, FIG. 2B describes various operations (e.g., 252-268) that may be performed by the controller 151 at 208 to analyze the EP signal. In various embodiments, certain operations may be omitted or added, certain operations may be combined, certain operations may be performed simultaneously, certain operations may be performed concurrently, certain operations may be split into multiple steps, certain operations may be performed in a different order, or certain operations or series of operations may be re-performed in an iterative fashion. It should be noted, other methods may be used, in accordance with embodiments herein.

The operations 252-266 shown in FIG. 2B may be performed by the controller 151 to analyze characteristics or a morphology of the EP signal. The morphology may correspond to a peak amplitude, latency, duration of positive/negative phases, a number of peaks, and/or the like of the corresponding EP signal. The morphology of the EP signal may be determined by the controller 151 and/or the sensing circuitry 158, for example, based on changes in subsequent electrical potential measurements from the sensing circuitry 158.

Beginning at 252, the controller 151 may determine slopes of the EP signal over time. For example, the controller circuit 151 may calculate a derivative of the EP signal to determine a slope of the EP signal over time. The slope represents a ratio of the change in electrical potential values (e.g., voltage) of the EP signal and the change in time. Optionally, the controller circuit 151 may determine a slope of the EP signal over time by continually determining the ratio between adjacent or successive electrical potential measurements of the EP signal.

At 254, the controller 151 may determine locations of one or more peaks within the EP signal based on slopes of the EP signal overtime. For example, the locations of the one or more peaks may correspond to a position on of the EP signal having a slope at and/or approximately zero.

At 256, the controller 151 may determine a number of peaks within the EP signal based on slopes of the EP signal overtime. For example, the controller 151 may determine the number of peaks within the EP signal corresponds to the number of positions of the EP signal having a slope at and/or approximately to zero.

At 258, the controller may determine a polarity (e.g., a positive peak, a negative peak) of one or more peaks within the EP signal based on the slopes of the EP signal over time. Optionally, based on changes in the magnitude and/or direction of the slopes, the controller 151 may determine a number (e.g., at 256) and location (e.g., at 254) of one or more peaks of the EP signal.

For example, the controller 151 may determine a number and magnitude of the peaks of the EP signal 1102 (FIG. 11) based on the slopes of the EP signal 1102 over time. The controller 151 may determine at 1150-1154 the slope of the EP signal 1102 is at and/or approximately zero, and correspond to peak locations of the EP signal 1102. The controller 151 may compare magnitudes of the slopes around the determined peaks to determine a polarity of the peak.

For example, the controller 151 may determine that the slope of the EP signal 1102 between 1154 and 1150 is negative, and a slope of the EP signal 1102 between 1150 and 1152 is positive. Based on the change in magnitude of the slope from negative to positive, the controller 151 may determine that the peak of the EP signal 1102 occurring at 1150 is a negative peak, such as the negative peak 1108.

Returning to FIG. 2B, at 260, the controller 151 may determine an amplitude of the peak by comparing the electrical potential value of the corresponding EP signal at the peak with a baseline value (e.g., common ground of the IPG 350). For example, the controller 151 determine the negative peak 1108 has an amplitude 1162 based on an electrical potential 1158 and a baseline value 1160. Optionally, the amplitudes of the peaks may be determined by the controller 151 based on peak values (e.g., apex, vertex of intersections of adjacent slopes) of the EP signal with respect to the baseline value. Amplitudes of the one or more peaks may correspond to the extent of activation of the corresponding target nerve fiber. For example, an EP signal with peaks having larger amplitudes may correspond to neuronal coherence of the target nerve fibers while smaller amplitudes may correspond to a lack of neuronal coherence or scrambling of the target nerve fibers.

At 262, the controller 151 may determine a peak-to-peak value by comparing the electrical potential values of two different peaks of the EP signal. For example, the controller 151 may determine a peak-to-peak value between the first positive peak 1110 and the negative peak 1108 of the EP signal 1102 by comparing the electrical potential 1156 of the first positive peak 1110 and the electrical potential 1158 of the negative peak 1108.

At 264, the controller 151 may determine one or more durations of the peaks of the EP signal. The duration of the peak may be based on points of the EP signal above the baseline value that form the peak. For example, the controller 151 may determine the duration of the first positive peak 1110 is from a first point 1164 of the EP signal at the baseline value 1160 associated with a positive slope to a second point 1166 of the EP signal at the baseline value 1160 associated with a negative slope that form the first positive peak 1110.

Optionally, the controller 151 may determine the duration of a peak based on adjacent peaks. For example, the controller 151 may determine a duration of the negative peak 1108 is from 1154 to 1152 corresponding to the first positive peak 1110 and the second positive peak 1112.

At 266, the controller 151 may determine latencies of one or more peaks of the EP signal. The latencies of the EP signal may be based on an action potential propagation speed of the target nerve fiber. For example, the controller 151 may determine a latency of the EP signal based on an amount of time a negative peak occurs with respect to a beginning of the corresponding communication window and/or preceding pulse. For example, the controller 151 may determine the latency of the peak 1108 is a difference in time from the pulse 760a to the time 1150. The latency may indicate the nerve fiber components activated during the burst. For example, an Aβ sensory fiber is larger than an Aδ sensory fiber and a C sensory fiber. Thus, an EP signal generated by the Aβ sensory fiber may travel faster and have a short latency relative to an EP signal generated by the Aδ sensory fiber and/or unmyelinated C sensory fiber. In another example, the Aδ sensory fiber is larger than the C sensory fiber. Thus, an EP signal generated by the Aδ sensory fiber may travel faster and have a low latency relative to an EP signal generated by the C sensory fiber.

At 268, the controller 151 may store the characteristics of the EP signal determined at one or more of the operations 252-266 on the memory 161. Optionally, the characteristics may be transmitted to the external device 160 by the communication circuitry 155.

Optionally, the EP signal analyzed at 208 may be based on an ensemble average of multiple EP signals each having similarly positioned analysis windows measured at different times. The number of EP signals used for the ensemble average may be determined by the controller 151 based on a signal to noise ratio. For example, the controller 151 may include more EP signals in an ensemble average with a lower signal to noise ratio compared to a higher signal to noise ratio.

In determining the ensemble average, the controller 151 may deliver a series of non-paresthesia stimulation waveforms and/or modified non-paresthesia stimulation waveforms over time, which correspond to a plurality of successive bursts (e.g., fifty). A portion of the bursts within the series may include similarly positioned analysis windows relative to the bursts, which are measured by the sensing circuitry 158. The controller 151 may average the EP signal measured at the analysis windows to determine the ensemble average EP signal, which may be used at 208.

For example, the controller 151 may deliver a series of non-paresthesia stimulation waveforms resulting in a hundred successive bursts delivered by the controller 151. During the series, the controller 151 may deliver a burst similar to the modified first burst 708 of FIG. 7 after a select number of successive bursts (e.g., every ten bursts, every twenty bursts) within the series.

The sensing circuitry 158 may measure multiple EP signals each corresponding to a similarly positioned analysis window with respect to or in relation to the burst, the analysis window 704, acquired at different times. The controller 151 may average the multiple EP signals to generate an ensemble average. A technical effect of the ensemble average may be a reduction in asynchronous measurements (e.g., noise, polarization artifacts, shifting positions of the lead) included within the analyzed EP signal.

It should be noted that in various embodiments, the select number of bursts may be randomly selected, predetermined based on a signal to noise ratio, or a sequence of select numbers stored on memory 161. Optionally, the select number of busts may be updated or changed by the controller 151 when a modified first burst 708 is delivered.

Returning to FIG. 2A, at 210, the controller 151 may determine whether the EP signal is within a threshold. The threshold may correspond to a predetermined threshold associated with a target EP signal defined by the SCS program. For example, the threshold may correspond to one or more characteristics of the target EP signal such as amplitude, latency, and/or duration of the peaks.

The controller 151 may compare the threshold with the EP signal to determine if adjustments in the SCS program parameters are required.

Additionally or alternatively, the controller 151 may determine if the EP signal is within a threshold based on a decay curve derived from previously measured EP signals. The decay curve may be used by the controller 151 to estimate the neural coherence produced by the non-paresthesia stimulation waveform. In connection with FIG. 3, the controller 151 may generate the decay curve 1314 based on multiple EP signals, such as the EP signals 1102-1106.

Figure 13:
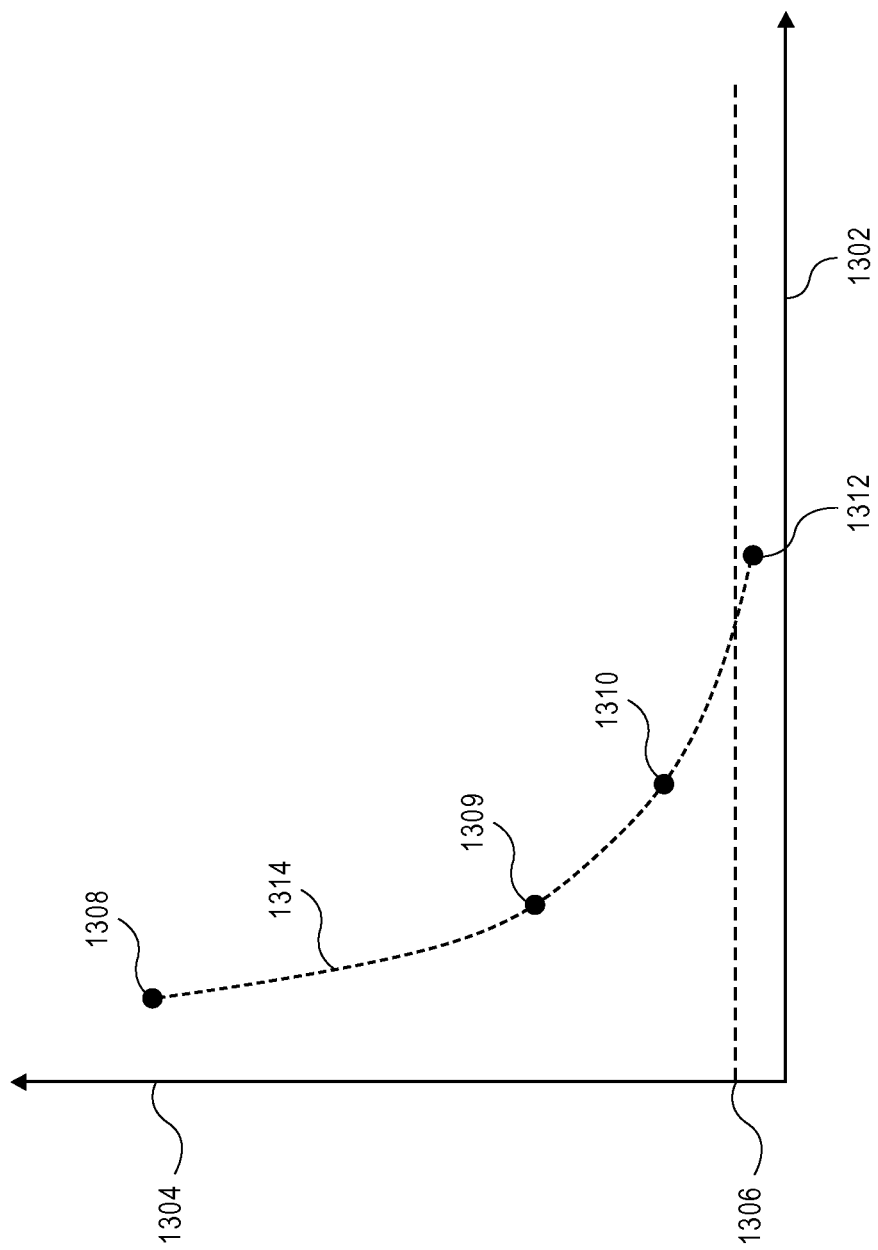
FIG. 13 illustrates a decay curve based on the evoked potential signals, in accordance with an embodiment.

FIG. 13 illustrates the decay curve 1314 based on amplitudes of the EP signals from 208 (FIG. 2), such as the EP signals 1102-1106. The amplitudes of the EP signals are shown as the plots 1308-1312. A horizontal axis 1302 corresponds to a position of the analysis window (e.g., the analysis window 762, the analysis window 704, the analysis window 706) or number of the pulse within the associated burst resulting in the EP signals. A vertical axis 1304 of FIG. 13 represents the amplitude of the EP signal represented by the plots 1308-1312. The controller 151 may compare the decay curve 1314 with a coherence threshold 1306. The coherence threshold 1306 may correspond to an amplitude of the target EP signal that lacks neural coherence.

For example, the controller 151 may determine that the EP signals associated with the plots 1308 and 1310 are not within the coherence threshold 1306. In another example, the controller 151 may determine that the EP signal associated with the plot 1312 is within the coherence threshold 1306. This can be used to define the minimum number of pulses in a burst required to sufficiently disrupt neuronal coherence.

Additionally or alternatively, the coherence threshold 1306 may be based on an asymptote of the decay curve 1314. For example, the controller 151 may calculate or fit an exponential curve to the decay curve 1314. Based on the calculated exponential curve, derived from the decay curve 1314, the controller 151 may calculate a corresponding asymptote. The controller 151 may determine the coherence threshold 1306 as a predetermined value above the asymptote. If the controller 151 determines the EP signal is not within the threshold, then at 212 (FIG. 2A), the controller 151 may adjust at least one therapy parameter to change the non-paresthesia stimulation waveform based on the activity data. The therapy parameter may correspond to a stimulation level of the non-paresthesia stimulation waveform (e.g., the non-paresthesia stimulation waveform 402, the modified non-paresthesia stimulation waveform 602, 702, 750, 802, 902, 904). For example, the controller 151 may execute a proportional-integral-derivative (PID) algorithm, which may determine an error rate or difference between the EP signal and the threshold. The controller 151 based on the PID may adjust an amplitude 420 and/or pulse width 412 of the pulses 404a-j, number of pulses within the first and second bursts 408 and 410, the inter-burst delay 406, the inter-burst pulse frequency 418, and/or the intra-burst frequency 414 of the non-paresthesia stimulation waveform 402 to reduce the difference or error rate between the threshold and the EP signal.

Figure 14:
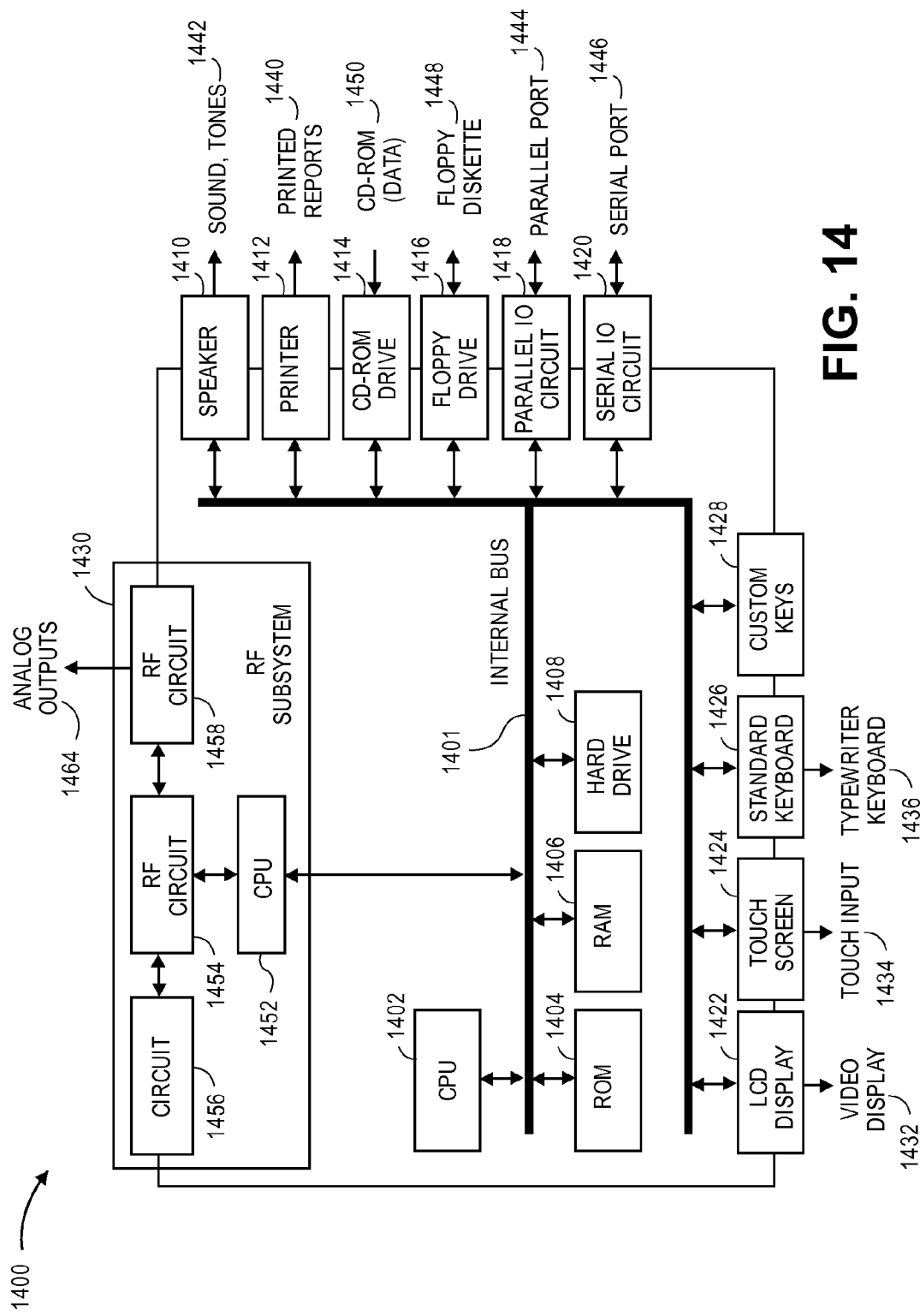
FIG. 14 illustrates a schematic block diagram of an external device, in accordance with an embodiment.

FIG. 14 illustrates a functional block diagram of an external device 1400, according to at least one embodiment, that is operated in accordance with the processes described herein and to interface with the NS system 100 as described herein. The external device 1400 may be similar to and/or the same as the external device 160. The external device 1400 may be a workstation, a portable computer, a tablet computer, a PDA, a cell phone and the like. The external device 1400 includes an internal bus 1401 that may connect/interface with a Central Processing Unit ("CPU") 1402, ROM 1404, RAM 1406, a hard drive 1408, a speaker 1410, a printer 1412, a CD-ROM drive 1414, a floppy drive 1416, a parallel I/O circuit 1418, a serial I/O circuit 1420, the display 1422, a touch screen 1424, a standard keyboard 1426, custom keys 1428, and an RF subsystem 1430. The internal bus 1401 is an address/data bus that transfers information between the various components described herein. The hard drive 1408 may store operational programs as well as data, such as stimulation waveform templates and detection thresholds.

The CPU 1402 typically includes a microprocessor, a microcontroller, or equivalent control circuitry, designed specifically to control interfacing with the external device 1400 and with the NS system 100. The CPU 1402 may include RAM or ROM memory, logic and timing circuitry, state machine circuitry, and I/O circuitry to interface with the NS system 100. The display 1422 (e.g., may be connected to the video display 1432). The display 1422 displays various information related to the processes described herein. The touch screen 1424 may display graphic information relating to the NS system 100 (e.g., stimulation levels, stimulation waveforms, evoked potential measurements) and include a graphical user interface. The graphical user interface may include graphical icons, scroll bars, buttons, and the like which may receive or detect user or touch inputs 1434 for the external device 1400 when selections are made by the user. Optionally the touch screen 1424 may be integrated with the display 1422. The keyboard 1426 (e.g., a typewriter keyboard 1436) allows the user to enter data to the displayed fields, as well as interface with the RF subsystem 1430. Furthermore, custom keys 1428, for example, may turn on/off the external device 1400. The printer 1412 prints copies of reports 1440 for a physician to review or to be placed in a patient file, and the speaker 1410 provides an audible warning (e.g., sounds and tones 1442) to the user. The parallel I/O circuit 1418 interfaces with a parallel port 1444. The serial I/O circuit 1420 interfaces with a serial port 1446. The floppy drive 1416 accepts diskettes 1448. Optionally, the serial I/O port may be coupled to a USB port or other interface capable of communicating with a USB device such as a memory stick. The CD-ROM drive 1414 accepts CD-ROMs 1450.

The RF subsystem 1430 includes a central processing unit (CPU) 1452 in electrical communication with RF circuitry 1454, which may communicate with both memory 1456 and an analog out circuit 1458. The analog out circuit 1458 includes communication circuits to communicate with analog outputs 1464. The external device 1400 may wirelessly communicate with the NS system 100 using a telemetry system. Additionally or alternatively, the external device 1400 may wirelessly communicate with the NS system 100 utilize wireless protocols, such as Bluetooth, Bluetooth low energy, WiFi, MICS, and/or the like. Alternatively, a hard-wired connection may be used to connect the external device 1400 to the NS system 100.

Optionally, the external device 1400 may transmit the stimulation database request to the IPG 150. For example, the user may instruct the external device 1400 to transmit a stimulation database request from the graphical user interface on the touch screen 1424, the keyboard 1426, or the like. The NS system 100 receives the request via the communication circuitry 155 (e.g., the RF subsystem 1430, RF circuitry 1454) and transmits the stimulation database stored on the memory 161 to the external device 1400.

The controller 151, the CPU 1402, and the CPU 1452 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 151, the CPU 1402, and the CPU 1452 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 151, the CPU 1402, and the CPU 1452 may execute a set of instructions that are stored in one or more storage elements, in order to process data. The storage elements may also store data or other information as desired or needed. The storage element may be in the form of an information source or a physical memory element within the controller 151, the CPU 1402, and the CPU 1452. The set of instructions may include various commands that instruct the controller 151, the CPU 1402, and the CPU 1452 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method to control non-paresthesia stimulation of nerve tissue of a patient, the method comprising:
    delivering a non-paresthesia stimulation waveform to at least one electrode located proximate to target nerve fibers, the non-paresthesia stimulation waveform including pulses arranged in at least first and second bursts separated by an inter-burst delay, wherein the pulses excite at least a portion of the corresponding target nerve fibers that enter a refractory state when excited;
    defining an analysis window that is positioned to occur at an intermediate point within at least one of i) the first burst or ii) the inter-burst delay, the analysis window positioned to overlap at least a trailing portion of the refractory state induced by the associated preceding pulses;
    during the analysis window, measuring evoked potential (EP) signals from the target nerve fibers, the EP signals generated in response to the pulses of the first burst;
    analyzing the EP signals to obtain activity data for select nerve fiber components; and
    adjusting at least one therapy parameter to change the non-paresthesia stimulation waveform based on the activity data.

2. The method of claim 1, where the first burst includes a first pulse and a last pulse, the method further comprising suppressing an intermediate pulse in the first burst and replacing the intermediate pulse with the analysis window such that the EP signals are measured at an intermediate point within the first burst after the first pulse and before the last pulse.

3. The method of claim 1, wherein each of the first and second bursts include at least four pulses separated by an inter-pulse delay, the method further comprising suppressing a pulse at a first location within the first burst and suppressing a pulse at a second location within the second burst, the first and second locations differing from one another, and replacing the pulses that are suppressed with corresponding analysis windows such that the EP signals are measured at different times relative to starting points of the first and second bursts.

4. The method of claim 1, further comprising defining multiple analysis windows and following the first and second bursts with a series of bursts, and shifting locations of the multiple analysis windows within the series of bursts.

5. The method of claim 4, further comprising, during the multiple analysis windows, measuring a series of EP signals from the target nerve fibers; and
    calculating a decay curve based from the EP signals and the series of EP signals.

6. The method of claim 4, further comprising, during the multiple analysis windows, measuring a series of EP signals from the target nerve fibers; and
    calculating an ensemble average of EP signals measured during the multiple analysis windows having the same location.

7. The method of claim 1, further comprising delivering a test pulse during the inter-burst delay, the test pulse separate and distinct from the first and second bursts, the defining operation including positioning the analysis window after the test pulse and before the second burst.

8. The method of claim 7, further comprising delivering a series of bursts with test pulses delivered during select inter-burst delays and shifting a position of the test pulses and corresponding analysis windows relative to an end of preceding bursts.

9. The method of claim 1, wherein the first and second bursts each include a series of pulses spaced at a select intra-burst pulse frequency, and wherein the first and second bursts are spaced at a select inter-burst frequency.

10. The method of claim 1, wherein the pulses are arranged in the first and second bursts to create a non-coherent neuronal activity pattern.

11. The method of claim 1, wherein the first burst includes first and second pulses timed such that the second pulse is delivered during a neuronal refractory period following the first pulse and only a subpopulation of neurons that have recovered from the refractory state will fire an action potential in response to the second pulse.

12. The method of claim 1, wherein the first burst includes first, second and third pulses timed over a course of the first burst so that different neurons within a population are excited at different times, and thereby show a lack of coherence.

13. The method of claim 1, wherein a series of bursts is delivered following the first and second bursts, and wherein the method further comprises defining multiple analysis windows within a portion of the series of bursts, the multiple analysis windows occurring at a second intermediate point positioned at the same location within the portion of the series of bursts as the intermediate point relative to the first burst.

14. A system to control non-paresthesia stimulation of nerve tissue of a patient comprising:
    an implantable pulse generator (IPG) electrically coupled to a first electrode, wherein the IPG is configured to deliver a non-paresthesia stimulation waveform to at least one electrode located proximate to target nerve fibers, the non-paresthesia stimulation waveform including pulses arranged in at least first and second bursts separated by an inter-burst delay, wherein the pulses excite at least a portion of the corresponding target nerve fibers that enter a refractory state when excited;

a memory device configured to store programmed instructions; and one or more processors, when executing the programmed instructions, perform the following operations:

defining an analysis window that is positioned to occur at an intermediate point within at least one of i) the first burst or ii) the inter-burst delay, the analysis window positioned to overlap at least a trailing portion of the refractory state induced by the associated preceding pulses;

during the analysis window, measuring evoked potential (EP) signals from the target nerve fibers, the EP signals generated in response to the pulses of the first burst;

analyzing the EP signals to obtain activity data for select nerve fiber components; and adjusting at least one therapy parameter to change the non-paresthesia stimulation waveform based on the activity data.

15. The system of claim 14, wherein the first burst includes a first pulse and a last pulse, the processor when executing the programmed instructions perform the additional operation of suppressing an intermediate pulse in the first burst and replacing the intermediate pulse with the analysis window such that the EP signals are measured at an intermediate point within the first burst after the first pulse and before the last pulse.

16. The system of claim 14, wherein each of the first and second bursts include at least four pulses separated by an inter-pulse delay, the processor performs an additional operation of suppressing a pulse at a first location within the first burst and suppressing a pulse at a second location within the second burst, the first and second locations differing from one another, and replacing the pulses that are suppressed with corresponding analysis windows such that the EP signals are measured at different times relative to starting points of the first and second bursts.

17. The system of claim 14, wherein the processor performs an additional operation of delivering a test pulse during the inter-burst delay, the test pulse separate and distinct from the first and second bursts, the defining operation including positioning the analysis window after the test pulse and before the second burst.

18. The system of claim 17, wherein the processor performs an additional operation of delivering a series of bursts with test pulses delivered during select inter-burst delays and shifting a position of the test pulses and corresponding analysis windows relative to an end of preceding bursts.

19. The system of claim 14, wherein the first burst includes first and second pulses timed such that the second pulse is delivered during a neuronal refractory period following the first pulse and only a subpopulation of neurons that have recovered from the refractory state will fire an action potential in response to the second pulse.

20. The system of claim 14, wherein the first burst includes first, second and third pulses timed over a course of the first burst so that different neurons within a population are excited at different times, thereby showing a lack of coherence.

* * * * *